US005658880A

United States Patent [19]
Dasgupta et al.

[11] Patent Number: 5,658,880
[45] Date of Patent: Aug. 19, 1997

[54] SIALIC ACID/FUCOSE BASED MEDICAMENTS

[75] Inventors: Falguni Dasgupta, San Leandro; John H. Musser, San Carlos; Daniel E. Levy, Oakland; Peng Cho Tang, Moraga, all of Calif.

[73] Assignee: Glycomed Incorporated, Alameda, Calif.

[21] Appl. No.: 289,715

[22] Filed: Aug. 12, 1994

Related U.S. Application Data

[63] Continuation-in-part of Ser. No. 78,949, Jun. 16, 1993, abandoned.

[51] Int. Cl.⁶ .................. A61K 31/715; A61K 38/14; C07H 3/06; C07K 2/00
[52] U.S. Cl. .................. 514/8; 514/2; 514/24; 514/25; 514/42; 514/43; 514/52; 514/53; 514/54; 514/61; 514/62; 530/322; 536/4.1; 536/17.2; 536/17.3; 536/17.4; 536/17.5; 536/17.6; 536/17.9; 536/18.1; 536/18.4; 536/18.7; 536/115; 536/116; 536/117; 536/118; 536/119; 536/120; 536/121; 536/122; 536/123.13
[58] Field of Search .................. 536/4.1, 17.2, 536/17.3, 17.4, 17.5, 17.6, 17.9, 18.1, 18.4, 18.7, 115, 116, 117, 118, 119, 120, 121, 122, 123.13; 530/322; 514/2, 8, 24, 25, 42, 43, 52, 53, 54, 61, 62

[56] References Cited

U.S. PATENT DOCUMENTS

| | | | |
|---|---|---|---|
| 4,849,513 | 7/1989 | Smith et al. | 536/26.6 |
| 5,138,044 | 8/1992 | Dasgupta | 536/18.5 |
| 5,143,712 | 9/1992 | Brandley et al. | 424/1.73 |
| 5,211,937 | 5/1993 | Brandley et al. | 424/1.73 |
| 5,296,594 | 3/1994 | Ratcliffe et al. | 536/53 |
| 5,316,913 | 5/1994 | Butcher et al. | 435/7.24 |
| 5,318,890 | 6/1994 | Rosen et al. | 435/7.24 |

FOREIGN PATENT DOCUMENTS

| | | |
|---|---|---|
| 0671408 | 9/1995 | European Pat. Off. . |
| WO90/13300 | 11/1990 | WIPO . |
| WO91/07993 | 6/1991 | WIPO . |

(List continued on next page.)

OTHER PUBLICATIONS

Kaila, N. et al., "Design and Synthesis of Novel Sialyl Lewis X Mimics," *Tetrahedr. Lett.*, vol. 36, No. 31, pp. 5503–5506 (1995).

Huang, H. et al., "Synthesis of Biologically Active Sialyl Lewis X Mimetic," *J. Org. Chem.*, vol. 60, pp. 3100–3106 (1995).

(List continued on next page.)

*Primary Examiner*—Gary L. Kunz
*Assistant Examiner*—Kathleen Kahler Fonda
*Attorney, Agent, or Firm*—Lyon & Lyon

[57] ABSTRACT

Compounds that exhibit selectin binding activity are described and have the following structural formula:

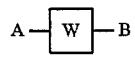

where W is selected from a group including structures a–d below

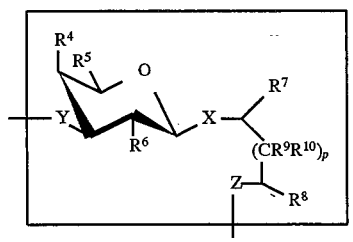

(a)

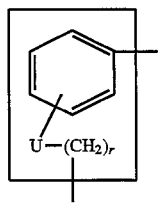

(b)

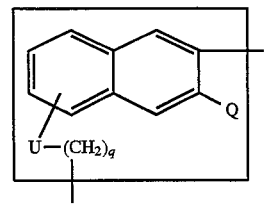

(c)

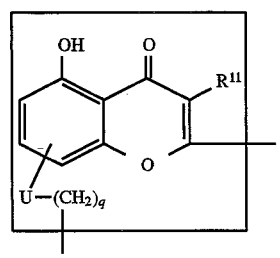

(d)

wherein p is an integer of from 0–2, q is an integer of from 0–3, and r is an integer of from 0–5;

A is selected from the group consisting of α and β forms of sialic acid, Kemp's acid, quinic acid, R and S forms of mandelic acid, R and S forms of glyceric acid, R and S forms of lactic acid, propionic and acetic acid, and esters and amides thereof, —$SO_3$, sulfonate, —$PO_3$, phosphonate, trifluoromethyl, diazine and triazine;

B is selected from a group consisting of α and β forms of fucose, arabinose and esters and substituted forms thereof wherein one or more of the OH groups is independently substituted with F, $N_3$, NHAc, NHCOCF$_3$. The remaining variable are described in the specification.

48 Claims, 6 Drawing Sheets

FOREIGN PATENT DOCUMENTS

WO91/19501 12/1991 WIPO.
WO91/19502 12/1991 WIPO.
WO92/07572 5/1992 WIPO.
WO92/09293 6/1992 WIPO.
WO92/14757 9/1992 WIPO.
WO92/16612 10/1992 WIPO.
WO92/18610 10/1992 WIPO.
WO93/00908 1/1993 WIPO.
WO93/00919 1/1993 WIPO.
9310796 6/1993 WIPO.

OTHER PUBLICATIONS

Uchiyama, T. et al. "Deisgn and Synthesis of Sialyl Lewis X. Mimetics," *J. Am. Chem. Soc.,* vol. 117, pp. 5395–5396 (1995).

Z. Szurmai et al., "Diethylene and Triethylene Glycol Spacers for the Preparation of Neoglycoproteins," *Acta Chim. Hungarica,* vol. 126, pp. 259–269 (1989).

T. Sugawara, "Synthesis of Omega–(Methoxycarbonyl) Alkyl and 9–(Methoxycarbonyl)–3,6–Dioxynonyl Glycopyranosides for the Preparation of Carbohydrate–Protein Conjugates," *Carbohydr. Res.,* vol. 230, pp. 117–149 (1992).

N.M. Allanson et al., "A Novel Mimic of the Sialyl Lewis X Determinant," *Tetrahedr. Lett.,* vol. 34, pp. 3945–3948 (1993).

F. Dasgupta et al., "Anti–Adhesive Therapeutics," *Expert Opinion on Investigational Drugs,* vol. 3, No. 7, pp. 709–724 (1994).

J.A. Ragan et al., "Synthesis of a Galactos–Fucose Disaccharide Mimic of Sialyl Lewis X," *Bioorg. Med. Chem. Lett.,* vol. 4, No. 21, pp. 2563–2566 (1994).

S. Hanessian, "Design and Synthesis of Glycomimetic Prototypes—A Model Sialyl Lewis X Ligand for E–Selectin," *Synlett,* pp. 768–770 (1994).

N.M. Allanson et al., "The Synthesis of Novel Mimics of the Sialyl Lewis X Determinant," *Tetrahedron: Assymetry,* vol. 5, No. 11, pp. 2061–2076 (1994).

J.C. Prodger et al., "Synthesis of a Novel Analogue of Sialyl Lewis X," *Tetrahedr. Lett.,* vol. 36, pp. 2339–2342 (1995).

Phillips et al., Science, 258:1130–1132 (1990).

Tyrrell et al., PNAS, 88:22:10372–10376 (1991).

Ball et al., ACS, 114:13:5449–5451 (1992).

DeFrees et al., "Ligand Recognition by E–Selectin: Analysis of Conformation and Activity of Synthetic Monomeric and Bivalent Sialyl Lewis X Analogs[1]," J. Am. Chem. Soc., 115:7549–7550 (1993).

Erbe et al., J. Cell. Biol., 120:5:1227–1235 (1993).

Lewinsohn et al., "Leukocyte–Endothelial Cell Recognition: Evidence of a Common Molecular Mechanism Shared by Neutrophils, Lymphocytes, and Other Leukocytes," J. Immunology, 138:12:4313–4321 (1987).

Aruffo, et al., "Molecular cloning of a CD28 cDNA by a high–efficiency COS cell expression system" Proc. Natl. Acad. Sci. USA, 84:8573–8577 (1987).

Lo et al., "Two Leukocyte Receptors (CD11a/CD18 and CD11b/CD18) Mediate Transient Adhesion to Endothelium by Binding to Different Ligands," J. Immunol., 143:10:3325–3329 (1989).

Dasgupta et al., "Anti–adhesive therapeutics: a new class of anti–inflammatory agents," Exp. Opin. Invest. Drugs 3(7):709–724 (1994).

Watson et al., "Neutrophil influx into an inflammatory site inhibited by a soluble homing receptor–IgG chimaera," Nature, 349:164–167 (1991).

Hession et al., "Endothelial leukocyte adhesion molecule 1: Direct expression cloning and functional interactions," Proc. Natl. Acad. Sci. USA, 87:1673–1677 (1990).

Ma et al., "Monoclonal Antibody to L–Selectin Attenuates Neutrophil Accumulation and Protects Ischemic Reperfused Cat Myocardium," 88:2:649–658 (1993).

Taylor et al., "Antithrombin–III Prevents the Lethal Effects of *Escherichia coli* Infusion in Baboons," Circulatory Shock, 26:227–235 (1988).

Phillips et al., "ELAM–1 Mediates Cell Adhesion by Recognition of a Carbohydrate Ligand, Sialyl–Le$^x$," Science, 250:1130–1132 (1990).

Arnaout, "Structure and Function of the Leukocyte Adhesion Molecules CD11/CD18," Blood, 75:5:1037–1050 (1990).

Walz et al., "Recognition by ELAM–1 of the Sialyl–Le$^x$ Determinant on Myeloid and Tumor Cells," Science, 250:1132–1135 (1990).

Johnston et al., "Cloning of GMP–140, a Granule Membrane Protein of Platelets and Endothelium: Sequence Similarity to Proteins Involved in Cell Adhesion and Inflammation," 56:1033–1044 (1989).

Larsen et al., "PADGEM Protein: A Receptor that Mediates the Interaction of Activated Platelets with Neutrophils and Monocytes," Cell, 59:305–312 (1989).

Aruffo et al., "CD62/P–Selectin Recognition of Myeloid and Tumor Cell Sulfatides," 67:35–44 (1991).

Osborn, et al., "Direct Expression of Vascular Cell Adhesion Molecule 1, a Cytokine–Induced Endothelial Protein That Binds to Lymphocytes," Cell, 59:1203–1211 (1989).

Taylor, Jr., et al., "Protein C Prevents the Coagulopathic and Lethal Effects of *Escherichia coli* infusion in the Baboon," J. Clin. Invest., 79:918–925 (1987).

Blackburn et al., "Gangliosides Support Neural Retina Cell Adhesion," Journl. of Biol. Chem., 261:6:2873–2881 (1966).

Polte et al., "cDNA for endothelial leukocyte adhesion molecule 1 (ELAM1): sequence differences," Nucleic Acids Res., 18:4:1083 (1990).

Tyrrell et al., "Structural requirements for the carbohydrate ligand of E–selectin," Proc. Natl. Acad. Sci. USA, 88:10372–10376 (1991).

Berg et al., "A carbohydrate domain common to both Sialy Le$^x$ is recognized by the Endothelial Cell Leukocyte Adhesion Molecule ELAM–1," J. Biol. Chem., 268:23:14869–14872 (1991).

Handa et al., "Selectin GMP–140 (CD62, PADGEM) binds to Sialosyl–Le$^a$ And Sialosyl–Le$^x$, and Sulfated Glycans Modulate This Binding," Biochem and Biophys. Res. Commun., 181:3:1223–1230 (1991).

Aruffo et al., "Granule membrane protein 140 (GMP140) binds to carcinomas and carcinoma–derived cell lines," Proc. Natl. Acad. Sci. USA, 89:2292–2296 (1992).

Lowe et al., "ELAM–1–Dependent Cell Adhesion to Vascular Endothelium Determined by a Transfected Human Fucosyltransferase cDNA," Cell, 63:475–484 (1990).

Gundel et al., "Endothelial Leukocyte Adhesion Molecule–1 Mediates Antigen–induced Acute Airway Inflammation and Late–phase Airway Obstruction in Monkeys," J. Clin. Invest., 1407–1411 (1991).

Mulligan et al., "Role of Endothelial–Leukocyte Adhesion Molecule 1 (ELAM–1) in Neutrophil–Mediated Lung Injury in Rats," J. Clin. Invest., 88:1396–1406 (1991).

Mulligan et al., "Protective effects of oligosaccharides in P–selectin–dependent lung injury," Nature, 364:149–151 (1993).

Bevilacqua et al., "Endothelial Leukocyte Adhesion Molecule 1: An Inducible Receptor for Neutrophils Related to Complement Regulatory Proteins and Lectins," Science, vol. 243:1160–1165 ((1989).

Tedder et al., "Isolation and Chromosomal Localization of cDNAs Encoding a Novel Human Lymphocyte Cell Surface Molecule, LAM–1," J. Exp. Med., 170:123–133 (1989).

Lasky et al., "Cloning of a Lymphocyte Homing Receptor Reveals a Lectin Domain," Cell, 56:1045–1055 (1989).

Buerke et al., "Sialyl Lewis$^x$–containing Oligosaccharide Attenuates Myocardial Reperfusion Injury in Cats," J. Clin. Invest., 93:1140–1148 (1994).

Erbe et al., "P– and E–Selectin Use Common Sites for Carbohydrate Ligand Recognition and Cell Adhesion," J. Cell Biol. 120:5:1227–1235 (1993).

Palabrica et al., "Leukocyte accumulation promoting fibrin deposition is mediated in vivo by P–selectin on adherent platelets," Nature, 359:848–851 (1992).

Turunen et al., "Sialyl Lewis$^x$– and L–selectin–dependent site–specific lymphocyte extravasation into renal transplants during acute rejection," Eur. J. Immunol. 24:1130–1136 (1994).

Allanson et al., "A Novel Mimic of the Sialyl Lewis x Determinant," Tetrahedron Lett., 34:24:3945–3948 (1993).

SIALIC ACID/FUCOSE BASED MEDICAMENTS

This application is a continuation-in-part of application Ser. No. 08/078,949 filed Jun. 16, 1993, now abandoned.

FIELD OF THE INVENTION

This invention relates generally to the field of medicinal chemistry, and specifically to medicaments that are characterized by their capacity to bind to one or more of the three known selectins; E, L, and P-selectins. The medicaments consist of substituted pseudo-oligosaccharides wherein three chemical moieties are covalently linked in the following order: sialic acid, or an analogue or derivative thereof, a spacer, and fucose or an analogue or derivative thereof. Such medicaments have significant applications for diagnosis or prophylactic or therapeutic treatment of certain diseases including cancer, autoimmunity, and inflammation.

BACKGROUND OF THE INVENTION

A large body of data has been accumulated that implicates a family of receptors, the selectins (LEC-CAMs), in certain diseases including cancer, autoimmunity, and in the inflammatory response. The three known members of this family, L-Selectin (LECAM-1, LAM-1, gp90MEL), E-Selectin (LECAM-2, ELAM-1) and P-Selectin (LECAM-3, GMP-140, PADGEM), each contain a domain with homology to the calcium-dependent lectins (C-lectins), an EGF-like domain, and several complement binding protein-like domains (Bevilacqua et al., *Science* (1989) 243:1160–1165; Johnston et al., *Cell* (1989) 56:1033–1044; Lasky et al., *Cell* (1989)56:1045–1055; Tedder et al., *J. Exp. Med.* (1989) 170.:123–133, Dasgupta et al., *Exp. Opin. Invest. Drugs* (1994) 3(7):709). It has been proposed that the selectins bind to particular ligands and that this binding accounts for their biological activity. Thus, drugs that interfere with or prevent binding of the ligands to the selectins will be useful medicaments for treating a variety of diseases.

For instance, adhesion of circulating neutrophils to stimulated vascular endothelium is a primary event of the inflammatory response. Recently, Buerke et al. have demonstrated the important role of selectins in inflammatory states such as ischemia-reperfusion injury in cats (Buerke, M. et al, *J. Clin. Invest.* (1994) 93:1140). Turunen et al. have demonstrated the role of $sLe^x$ and L-selectin in site-specific lymphocyte extravasation in renal transplants during acute rejection (Turunen, J. P. et al, *Eur. J. Immunol.* (1994) 24:1130). P-selectin has been shown to be centrally involved particularly as related to acute lung injury. Mulligan et al. have reported strong protective effects using anti-P-selectin antibody in a rodent lung injury model. (Mulligan, M. S. et al., *J. Clin. Invest.* (1991)90:1600, Mulligan, M. S. et al., *Nature* (1993) 364:149). A central role of P-selectin in inflammation and thrombosis has been demonstrated by Palabrica et at (Palabrica, T. et al., *Nature* (1992) 359:843).

E-selectin is particularly interesting of the three selectins because of its transient expression on endothelial cells in response to IL-1 or TNF (Bevilacqua et al., Science (1989) 243:1160). The time course of this induced expression (2–8 h) suggests a role for this receptor in initial neutrophil extravasation in response to infection and injury. Indeed, Gundel et al. have shown that antibody to E-selectin blocks the influx of neutrophils in a primate model of asthma and thus is beneficial for preventing airway obstruction resulting from the inflammatory response. (Gundel R. H. et al., *J. Clin. Invest.* (1991) 88:1407).

Several different groups have published papers regarding E-selectin ligands. Lowe et al., (1990) demonstrated a positive correlation between E-selectin dependent adhesion of HL-60 cell variants and transfected cell lines, with their expression of the sialyl Lewis x ($sLe^x$) oligosaccharide, NeuNAc α-2-3-Gal-β1-4(Fuc α-1-3)-GlcNAc. By transfecting cells with plasmids containing an α-(1,3/1,4) fucosyltransferase, they were able to convert non-myeloid COS or CHO lines into $xLe^x$-positive cells that bind in an E-selectin dependent manner. Walz et al., (1990) were able to inhibit the binding of a E-selectin-lgG chimera to HL-60 cells with a monoclonal antibody directed against $sLe^x$ or by glycoproteins with the $sLe^x$ structure, but could not demonstrate inhibition with CD65 or CD15 antibodies. Both groups concluded that the $sLe^x$ structure is the ligand for E-selectin.

Information regarding the DNA sequences encoding endothelial cell-leukocyte adhesion molecules are disclosed in PCT published application WO90/13300 published Nov. 15, 1990 incorporated herein by reference. The PCT publication cites numerous articles which may be related to endothelial cell-leukocyte adhesion molecules. The PCT publication claims methods of identifying E-selectin ligands, as well as methods of inhibiting adhesion between leukocytes and endothelial cells using such ligands and specifically refers to MILAs which are described as molecules involved in leukocyte adhesion to endothelial cells. Recent publications regarding selectin ligands describe the use of L-selectin as an indicator of neutrophil activation (Butcher et al., U.S. Pat. No. 5,316,913 issued May 31, 1994), and assays for inhibition of leukocyte adhesion (Rosen et al., U.S. Pat. No. 5,318,890 issued Jun. 7, 1994).

As alluded to above, the ligand for E-selectin, $sLe^x$, consists of at least sialic acid, fucose, and lactose. Lactose consists of galactose and glucose. Sialic acid and fucose are bound to the galactose and glucose moieties of lactose, respectively. Ligands that bind to the other selectins share similar structural features. Considering the obvious medical importance of selectin ligands, significant effort has been, and continues to be expended to identify the critical physical/chemical parameters associated with selectin ligands that enhance, or that are required for their activity (DeFrees, S. A., et al, *J. Am. Chem., Soc.*, (1993) 115:7549). In no small part this effort is being driven by the need to have selectin ligands that are inexpensive to produce (see U.S. Pat. No. 5,296,594 issued Mar. 22, 1994, Allanson, N. M. et al., *Tetrahedron Lett.*, (1993) 34:3945.). It is generally thought that it will be commercially prohibitively expensive to produce naturally occurring $sLe^x$ by either enzymatic or chemical synthesis because of the number of sophisticated reactions involved.

SUMMARY OF THE INVENTION

A first object of the invention is the description of medicaments that are selectin ligands that bind to certain selectins, and that are cost effective to synthesize.

A second object of the invention is the description of medicaments that are selectin ligands that bind to certain selectins wherein the ligands lack the lactose core structure of sLewis$^x$ (sLe$^x$), and have substituted in its place a spacer moiety. Relative to sLe$^x$, such medicaments are cost effective to synthesize. Such invention compounds are represented by the following general structural formula I:

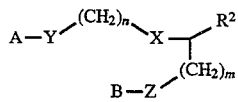
(I)

wherein m and n are independently an integer of from 1 to 5, Y and Z are independently a connecting moiety preferably —$CH_2$—, —O—, —S—, —SO—, —$SO_2$—, or —$NR^1$ (wherein $R^1$ is H or an alkyl containing 1 to 4 carbon atoms); X is a connecting moiety preferably —O—, —S—, —SO—, —$SO_2$—, or —$NR^1$—; and —$R^2$ may be —$R^1$ or any moiety which does not interfere with the three-dimensional configuration of A or B so as to substantially interfere with selectin binding and is preferably —$OR^1$, —$SR^1$, —$N_3$, and —$N(R^1)_2$, and A may be either α or β forms of sialic acid, Kemp's acid, quinic acid, R and S forms of mandelic acid, R and S forms of glyceric acid, R and S forms of lactic acid, propionic acid and acetic acid, and esters thereof, —$SO_3$ and —$PO_3$, with the proviso that when A is —$SO_3$ or —$PO_3$, Y is one of —$CH_2$—, —O— and —$NR^1$; and B is preferably α or β form of fucose, arabinose and esters and substituted forms thereof wherein one or more of the —OH groups is independently —F, or —$N(R^3)_2$ wherein —$R^3$ is an alkyl contain 1 to 5 carbons; and the general structural formula II:

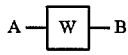

where W includes structures a–d below

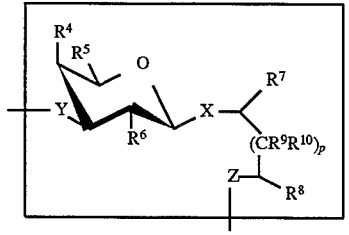
(a)

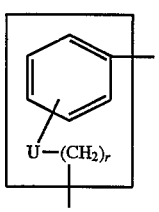
(b)

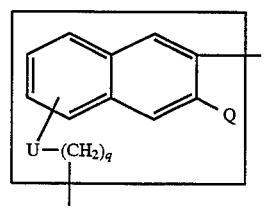
(c)

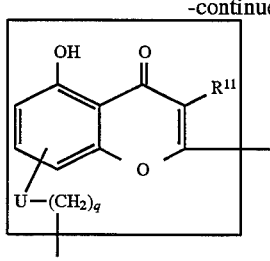
(d)

wherein p is an integer of from 0–2, q is an integer of from 0–3, and r is an integer of from 0–5;

A preferably includes α and β forms of sialic acid, Kemp's acid, quinic acid, R and S forms of mandelic acid, R and S forms of glyceric acid, R and S forms of lactic acid, propionic and acetic acid, and esters and amides thereof, —$SO_3$, sulfonate, —$PO_3$, phosphonate, trifluoromethyl, diazine and triazine;

B preferably includes α and β forms of fucose, arabinose and esters and substituted forms thereof wherein one or more of the OH groups may independently be substituted with F, $N_3$, NHAc, NHCOCF$_3$;

X, Y, Z=$CH_2$, N, O, S, SO, $SO_2$;

U=O or —$CH_2$;

Q=H or —X—$(CH_2)_q$B;

$R^4$=H, OH, F;

$R^5$=H, $CH_2$—$R^4$;

$R^6$=H, OH, NHAc, NHCOCF$_3$;

$R^7$ and $R^8$ may independently=H, —COR$_{12}$, —$CH_2$—O—$(CH_2)_s$—$SO_2$—$(CH_2)_s$—NHG, —$CH_2$—O—$(CH_2)_s$—NH—$(CH_2)_s$—CH(NHG)—COOR, —$CH_2$—O—$(CH_2)_s$—CHO, —$CH_2$—O—$(CH_2)_s$—(CHR$^{13}$)$_s$—(CH$_2$R$^{13}$), wherein s is an integer of from 1–10, or $R^7$ and $R^8$ taken together form a five or six membered ring, with the proviso that p=0, said ring optionally containing up to two heteroatoms consisting of N, O and S;

$R^9$, $R^{10}$ are independently H or OH, or $R^9$ and $R^{10}$ taken together is an oxo group;

$R^{11}$=H, 1–6C alkyl, halogen, OH, O-alkyl, or O-aryl;

$R^{12}$=OH, 2–10C alkoxy chains, 2–10C alkylamines, peptides, OM where M is a counterion, preferably a metal ion;

$R^{13}$=OCO—$(CH_2)_t$—$CH_3$, wherein t is an integer of from 3–18; and

G=a peptide, —COR$^{14}$ or —$SO_2R^{14}$, wherein $R^{14}$=an aryl, alkyl, alkenyl or alkynyl group.

A third object of the invention is a description of certain novel medicaments that incorporate newly discovered physical/chemical properties associated with sLe$^x$, such that the medicaments have a three-dimensionally stable configuration for the presentation of the functional groups of sLe$^x$, sialic acid and fucose that facilitates binding between those groups and the selectins.

A fourth object of the invention is to provide a composition comprising selectin ligand medicaments bound to a detectable label and/or bound to a pharmaceutically active drug such as an anti-inflammatory drug.

A fifth object of the invention is to provide a pharmaceutical formulation containing selectin ligand medicaments which is useful in treating certain diseases.

A sixth object of the invention is to provide a description of methods to treat or diagnose disease.

A seventh object of the invention is to provide compositions and methods to determine the site of inflammation by administering labeled formulations of the type referred to above.

Another object of the invention is that the ligands can be labeled and the labeled ligands used in an assay to detect the presence of selectins in a sample.

These and other objects, advantages and features of the present invention will become apparent to those persons skilled in the art upon reading the details of the synthesis, structure, formulation and usage as more fully set forth below.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF THE INVENTION

Figure 1:
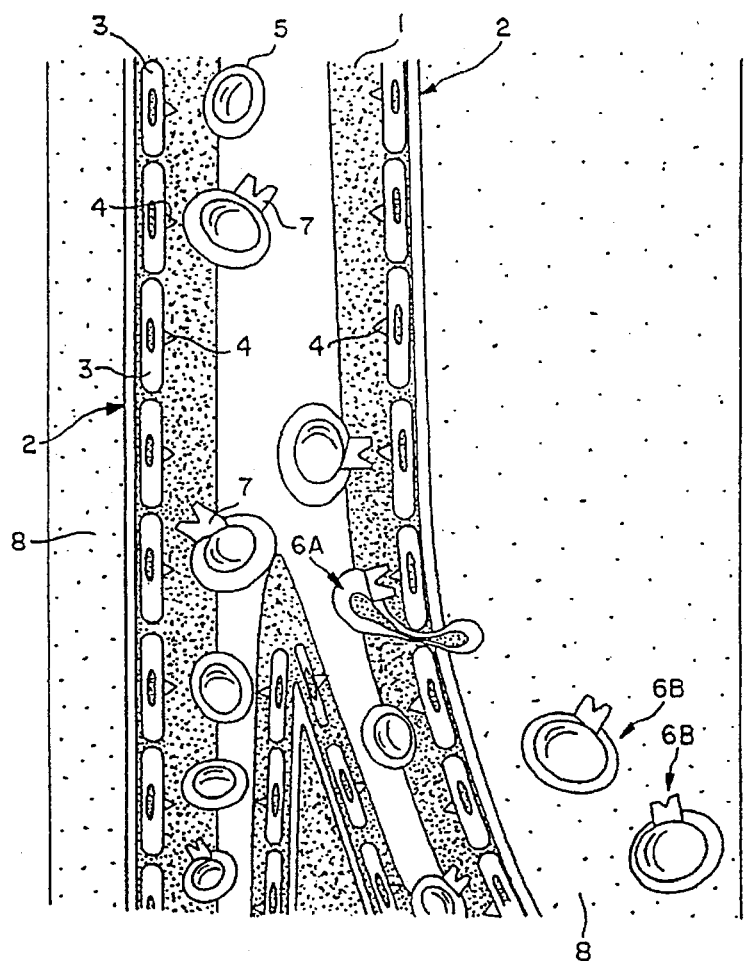
FIG. 1 is a cross-sectional schematic view showing the interaction between white blood cells and activated endothelial cells.

Throughout the description of the invention, reference is made to certain publications including scientific articles and patents or patent applications. It is the intent that each of these publications be incorporated by reference when referred to in the specification.

Before the present invention compounds and compositions containing such and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "a tethered compound" includes mixtures of such compounds, reference to "an E-selectin", "a P-selectin", or "a L-selectin" includes reference to respective mixtures of such molecules, reference to "the formulation" or "the method" includes one or more formulations, methods and/or steps of the type described herein and/or which will become apparent to those persons skilled in the art upon reading this disclosure and so forth.

Some standard abbreviations used in connection with the present invention include: BSA, bovine serum albumin; DEAE, diethylaminoethyl; DMSO, dimethylsulfoxide; DMF, N,N-dimethylforamide; DCE, dichloroethane; E-selectin or ELAM-1, endothelial/leukocyte adhesion molecule-1; HPTLC, high performance thin layer chromatography; L-selectin or LECAM-1, leukocyte/endothelial cell adhesion molecule-1; MOPS, 3-[N-Morpholino]-propanesulfonic acid; NANA, N-acetylneuraminic acid; PVC, polyvinylchloride; TLC, thin layer chromatography; TFA, trifluoro-acetic acid; Tris, tris (hydroxy-methyl) aminomethane.

DEVELOPMENT OF THE INVENTION

It is worth noting that while the invention compounds were selected for their capacity to bind to certain selectins, and that therefore this property contributes to their medical activity, it cannot, however, be excluded that they are also exerting their favorable medical effects, either in parallel or in tandem, through additional mechanisms of action. Thus, the skilled practitioner of this art will appreciate that a key aspect of the subject invention is the description of novel medicaments, and that Applicants intend not to be bound by a particular mechanism of action that may account for their prophylactic or therapeutic effects.

E-selectin has a lectin like domain that recognizes Sialyl Lewis (sLe$^x$) tetrasaccharide as shown below in Structure III.

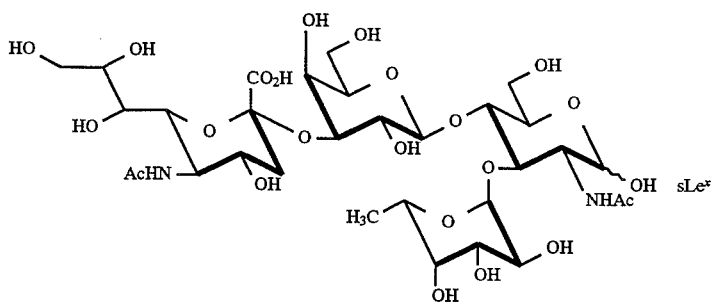

The ability of sLe$^x$ to E-selectin is described by Lowe et al., *Cell* (1990) 63:475; Phillips et al., *Science* (1990) 250:1130; Walz et al., *Science* (1990) 250:1132; and Tyrrell et al., *Proc. Natl. Acad. Sci. USA* (1991) 88:10372.

It has also been shown (Berg et al., *J Biol Chem* (1991) 265:14869; Handa et al., *Biochem Biophys Res Commun* (1991) 181:1223) that both E-selectin and P-selectin recognize the isomeric tetrasaccharide sLe$^a$ shown below as Structure IV.

compounds, such as those described and claimed herein, that maintain their selectin binding activity. While 4 to 12 is the preferred number of atoms, most preferred is 6 to 8 atoms as shown in the figure below.

For instance, a close structural examination of sLe$^x$ (shown in III) or a modification thereof wherein R=OH (sLe$^x$ Glc) indicates that the epitopes i.e., α-Neu5Ac and L-Fucose, are linked through six atoms (Nos. 1–6) or eight atoms (Nos. i–viii) as shown in Structure III (a) below

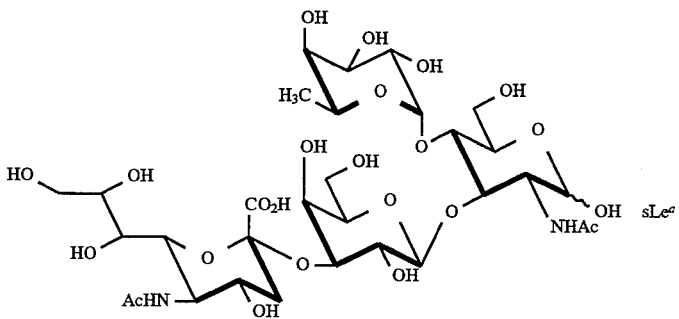

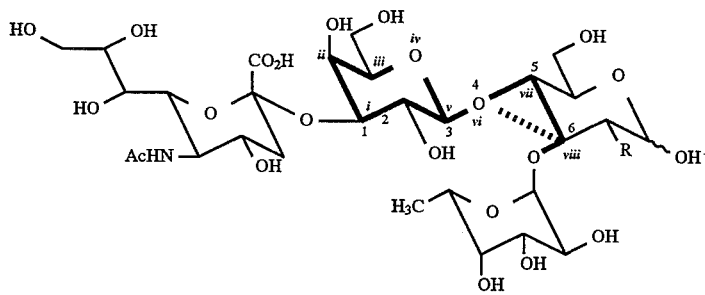

wherein R is —NHAc or —OH.

Based on this discovery, we deduced that the corresponding epitopes on the lectin domain of E-selectin, and the other selectins, are spaced in a similar three-dimensional configuration such that maintenance of the 6 to 8 atoms in the ligand structure would yield active ligands that are markedly different in structure from the naturally occurring ligand. The 4 to 12 atoms excludes those defined as "Y" and "Z" in formula I.

Additionally, we postulated that replacement of the lactose core with a partially or completely rigid core, while still juxtaposing the two functional epitopes in space in a way A key step in making the invention compounds was the realization that both sLe$^x$ and sLe$^a$ share a structural similarity in their three dimensional arrangements. Specifically, we observed that sialic acid and fucose, two functional epitopes in these tetrasaccharides, are juxtaposed in space in a way suitable for recognition by the selectins. Most importantly, for both tetrasaccharides we identified 4 to 12 atoms associated with the lactose core of the tetrasaccharides that functionally separate sialic acid from fucose. We postulated that replacement of these atoms would lead to suitable for recognition by the selectins, would lead to compounds, such as those described and claimed herein, that maintain their selectin binding activity.

Using these insights, we then designed certain selectin ligands. This has been done by attaching sialic acid and L-fucose as such, or analogs or derivatives thereof, through six or eight atoms to provide a series of compounds shown as structural formulae I and II. This series of compounds is designed to competitively inhibit selectins from binding to their natural ligands. These compounds can be combined with pharmaceutically acceptable excipients to provide pharmaceutical compositions useful in a wide range of treatments.

The structures that contain the appropriate reactive functions can be reacted with suitably protected hydrophobic carriers like ceramide or a ceramide mimic, steroids, diglycerides or phospholipids to form other medically useful molecules.

The compounds can act as antagonist ligand molecules, i.e. biochemical blocking agents by binding to selectins and preventing circulating neutrophils from binding to endothelial cells, thereby preventing a primary event involved in certain diseases, including the inflammatory response. Agonist ligands have the opposite effect.

The compounds of the present invention are designed to provide a three-dimensionally stable configuration for functional groups on sialic acid and fucose moieties so as to allow for binding between those groups and receptors on natural selectins. The compounds are represented by the following general structural formula I:

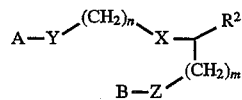

wherein m and n are independently an integer of from 1 to 5, Y and Z are independently a connecting moiety preferably —$CH_2$—, —O—, —S—, —SO—, —$SO_2$—, or —$NR^1$ (wherein $R^1$ is H or an alkyl containing 1 to 4 carbon atoms); X is a connecting moiety which is preferably —O—, —S—, —SO—, —$SO_2$—, and —$NR^1$—; and —$R^2$ may be —$R^1$ or any moiety which does not interfere with the three-dimensional configuration of A or B so as to substantially interfere with selectin binding and is preferably —$OR^1$, —$SR^1$, —$N_3$, and —$N(R^1)_2$, and A and B are as shown in structures V and VI respectively or bioisosteres thereof;

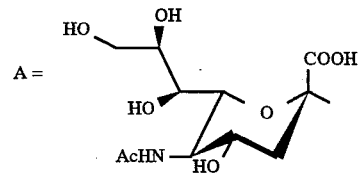

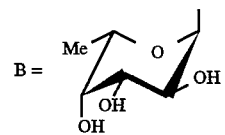

and the general structural formula II:

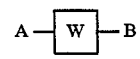

where W is selected from a group including structures a–d below

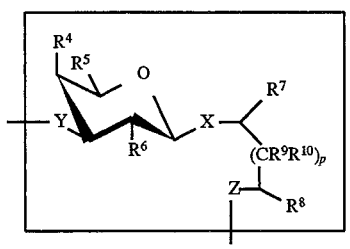

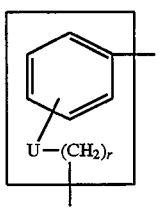

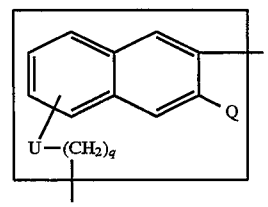

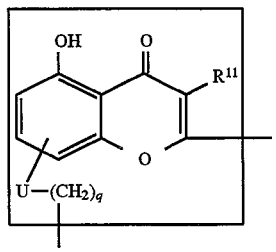

wherein p is an integer of from 0–2, q is an integer of from 0–3, and r is an integer of from 0–5;

A is preferably the α or β form of sialic acid, Kemp's acid, quinic acid, R and S forms of mandelic acid, R and S forms of glyceric acid, R and S forms of lactic acid, propionic and acetic acid, and esters and amides thereof, —$SO_3$, sulfonate, —$PO_3$, phosphonate, trifluoromethyl, diazine and triazine;

B is preferably the α or β form of fucose, arabinose and esters and substituted forms thereof wherein one or more of the OH groups is independently substituted with F, $N_3$, NHAc, $NHCOCF_3$;

X, Y, Z=$CH_2$, N, O, S, SO, $SO_2$;

U=O or —$CH_2$;

Q=H or —X—$(CH_2)_q$B;

$R^4$=H, OH, F;

$R^5$=H, $CH_2$—$R^4$;

$R^6$=H, OH, NHAc, $NHCOCF_3$;

$R^7$ and $R^8$=H, —$COR^{12}$, —$CH_2$—O—$(CH_2)_s$—$SO_2$—$(CH_2)_s$—NHG, —$CH_2$—O—$(CH_2)_s$—NH—$(CH_2)_s$—CH(NHG)—COOR, —$CH_2$—O—$(CH_2)_s$—CHO, —$CH_2$—O—$(CH_2)_s$—$(CHR^{13})_s$—$(CH_2R^{13})$, wherein s is an integer of from 1–10, or $R^7$ and $R^8$ taken together form a five or six membered ring, with the proviso that p=0, said ring optionally containing up to two heteroatoms consisting of N, O and S;

$R^9$, $R^{10}$ are independently H or OH, or $R^9$ and $R^{10}$ taken together is an oxo group;

$R^{11}$=H, 1–6C alkyl, halogen, OH, O-alkyl, or O-aryl;

$R^{12}$=OH, 2–10C alkoxy chains, 2–10C alkylamines, peptides, OM where M is a counterion, preferably a metal ion;

$R^{13}$=OCO—(CH$_2$)$_t$—CH$_3$, wherein t is an integer of from 3–18; and

G=a peptide, —COR$^{14}$ or —SO$_2$R$^{14}$, wherein R$^{14}$=an aryl, alkyl, alkenyl or alkynyl group.

The compounds of structural formulae I and II can be bound to known drugs, for example anti-inflammatory drugs so as to target the drug-selectin ligand complex to a particular site of disease. Additionally, these compounds can be formulated to provide compositions useful in assaying a sample for the presence of selectins such as E, L and/or P-selectin, or to detect the site of inflammation in a patient, or to treat acute inflammation (or treating the inflammatory symptoms of certain diseases) or other diseases involving the interaction of selectins on appropriate cell types.

In the general structural formula I, $R^2$ has been generally defined to be any moiety which, when attached at the $R^2$ position, will not substantially interfere with the ability of the molecule as a whole to bind to a selectin receptor. More specifically, $R^2$ may be an organic compound which contains hydrogen and carbon atoms alone or in combination with O, N and/or P. Specific examples of $R^2$ include:

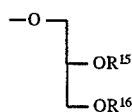

wherein $R^{15}$ and $R^{16}$ are independently an alkyl, or alkenyl, preferably an alkyl containing 1–6 carbons or containing 12 to 18 carbons;

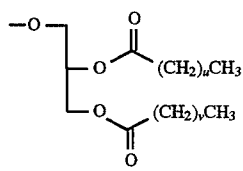

wherein u and v are each independently an integer of from 15 to 24 and wherein the alkyl group may be saturated or unsaturated;

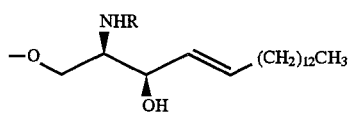

wherein R is —CO(CH$_2$)$_w$CH$_3$, wherein w=10–16; or

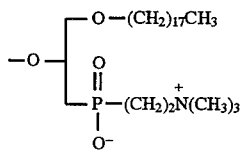

or

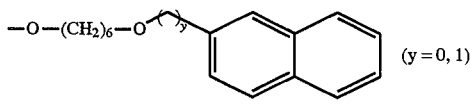 (y = 0, 1)

or

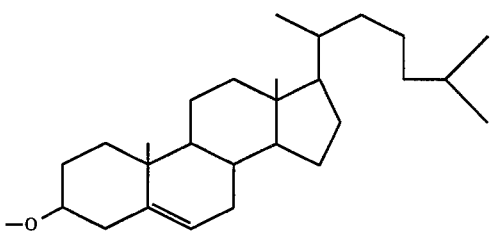

The preferred examples of A and B are shown respectively in formula V and VI. Other examples of A include α or β or other analogues or derivatives of sialic acid other than the N-acetyl neuraminic acid residue shown in formula V, Kemp's acid, quinic acid, R and S forms of mandelic acid, R and S forms of glyceric acid, R and S forms of lactic acid, propionic and acetic acid, and esters and amides thereof, —SO$_3$, —PO$_3$. The synthesis of certain analogues of sialic acid is described in U.S. Pat. No. 5,138,044.

Preferred forms of B are the α and β forms of L-fucose as shown in formula VI. The moiety B also includes substituted forms of the following fucose structure VI (a):

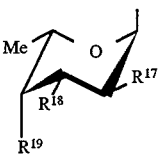

wherein Me is a methyl group, $R^{17}$, $R^{18}$ and $R^{19}$ are each independently —OH, —F, —N(R$^1$)$_2$ (wherein R$^1$ is an alkyl containing 1 to 5 carbon atoms). Other moieties for B include modified fucosides such as corresponding carboxylic analogues of fucose; inositol; substituted inositol; imidazole; substituted imidazole; benzimidazole; substituted benzimidazole; Guanidine; substituted butane; wherein substituents include —CH$_2$, —CHR$^{17}$, —CHR$^{18}$, CH$_2$R$^{19}$ and R$^{17}$, R$^{18}$ and R$^{19}$ are independently OH, F or —N(R$^1$)$_2$, pentaerythritol and substituted pentaerythritol.

Assaying Compounds of Formula I and II

The compounds of formulae I and II can be tested for their ability to bind to a selectin receptor and/or block the binding site of the receptor and thereby prevent a natural ligand from binding to the selectin receptor. A generalized procedure for testing the compounds of formulae I and II is given below.

An ELISA assay is preferably used that employs recombinant fusion proteins composed of extracellular portions of the human selectins joined to human immunoglobulin heavy chain CH$_3$, CH$_2$, and hinge regions. See, for example, Walz et al., *Science* (1990) 250:1132; Aruffo et al., *Cell* (1991) 67:35; Aruffo et al., *Proc. Natl. Acad. Sci. USA.* (1992) 89:2292. The assay is well known in the art, and generally consists of the following three steps:

I. 2,3 sLe$^x$ glycolipid (25 picomole/well) was transferred into microtiter wells as solutions and then evaporated off. Excess, which remained unattached, was washed off with water. The wells were then blocked with 5% BSA at room temperature for an hour and then washed with PBS containing 1 mM calcium.

II. Preparation of "multivalent" receptor of the Selectin-IgG chimera was carried out by combining the respective chimera (1 µg/mL) with biotin labelled goat F(ab')$_2$ anti-human IgG (Fc specific) and streptavidin-alkaline phosphatase diluted 1:1000 in 1% BSA-PBS (1 mM calcium) and incubating at 37° C. for 15 min. This allowed the soluble multivalent receptor complex to form. III. Potential inhibitors such as the compounds of formula I or II were allowed to react with the soluble receptor at 37° C. for 45 min. This test assumes that optimal binding, between the soluble phase receptor complex and the inhibitor (non natural ligand), would have occurred within this time frame. This solution was then placed in the microtiter wells that were prepared in step I. The plate was incubated at 37° C. for 45 minutes to allow the soluble receptor to bind to its natural ligand. In the presence of a strong inhibitor only a few receptors should be free to bind to the microtiter plate coated with the natural ligand.

The positive control is the signal produced by the soluble receptor when it is allowed to react with 2,3 sLe$^x$ glycolipid in the microtiter wells in the absence of any inhibitor. This positive control was considered 100% binding. The signal produced by the receptor that had been previously treated with an inhibitor (recorded as O.D.), was divided by the signal produced by the positive control and multiplied by 100 to calculate the % receptor bound to the well in the presence of the inhibitor. The reciprocal of this number is the % inhibition.

It is important to note that invention compounds include those having sialic acid and fucose separated by 4–12 atoms, or sialic acid or analogs or derivatives of sialic acid separated by 4–12 atoms bound to fucose or analogs or derivatives thereof.

Referring now to FIG. 1, a cross-sectional view of a blood vessel 1 is shown. The vessel wall 2 is lined internally with endothelial cells 3. The endothelial cells 3 can be activated causing the cells 3 to synthesize E or P-selectin which is displayed in FIG. 1 as a triangular surface receptor 4. Both red blood cells 5 and white blood cells (6A, 6B) flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
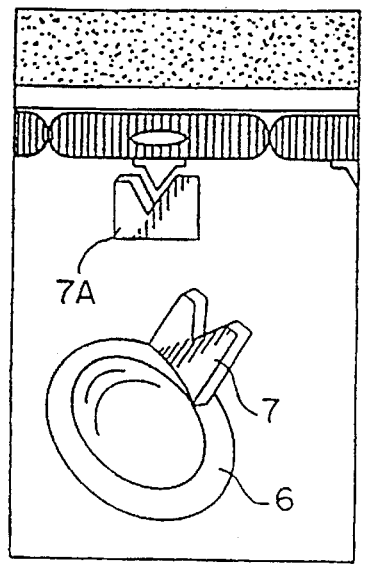
FIG. 2 is a cross-sectional schematic view showing how compounds of the invention would be used as pharmaceuticals to block E-selectin.

An important aspect of the present invention can be described by referring to FIG. 2. The compounds of a formulae I and II are shown as 7A and can adhere to a selectin such as E, L and/or P-selectin by themselves and can be formulated into pharmaceutical compositions, which when administered will effectively block the E, L and/or P-selectin and prevent the adhesion of a ligand 7 connected to a white blood cell 6. By administering pharmaceutically effective amounts of the compounds 7A, some, but not all, of the white blood cells will not reach the surrounding tissue. By slowing the rate at which the white blood cells reach the surrounding tissue, inflammation can be prevented and/or alleviated.

It is known that for an acute inflammatory response to occur, circulating neutrophils must bind to and penetrate the vascular wall and access the site of injury. Several molecules have been implicated in this interaction, including a family of putative carbohydrate ligands and their receptors. One molecule that was previously identified is the endogenous carbohydrate ligand for E-selectin. The present invention provides a family of molecules which bind as the endogenous ligands and thereby block other selectin receptors such as E, L and P-selectin receptors.

The compounds of formulae I and II may also be labeled using standard radioactive, fluorescent, enzymic or other label for analytical or diagnostic purposes. In general, the significant portion of the compounds of formula I is the compound shown; the embodiments of the substituent R$^2$ will depend on the intended use. Suitable embodiments for this substituent will be apparent to those skilled in this art.

Preferred embodiments of the ligands of the invention are those wherein the substituent represented by A or B is an N-acetylneuramyl residue and B is fucose.

In order for a ligand of the invention to bind to a selectin receptor such as an E, L and/or P-selectin receptor the ligand need not include the identical atoms in the identical configuration as per structural formulae I and II but must have (1) a relatively stable three dimensional conformation as shown in formulae I and II, or (2) a substantially equivalent configuration to that shown in formula I or II. The equivalency of any other ligand will relate to its physical three dimensional structure and the electron configuration of the molecule, and in particular the charge related characteristics presented by the groups present on the A and B moieties shown in formulae IV and V.

Assay to Identify Ligand (General)

Candidate ligands can be assayed for their ability to adhere to E, L or P-selectin. The method comprises attaching candidate ligands of formula I or II to a substrate surface and then contacting the substrate surface thereon with recombinant cells, that are genetically engineered to express high levels of E, L or P-selectin, for a sufficient time to allow the cells to adhere to the substrate bearing the candidate ligand. Thereafter, centrifugal force or other appropriate methodology is applied so as to separate away the cells which do not adhere to the substrate. Candidate ligands which adhere to E, L or P-selectin, respectively, are determined via the labels on the cells. Such molecules are isolated, characterized, and their structure specifically identified.

Radiolabeled COS cells expressing cell surface E, L and/or P-selectin can be used as probes to screen compounds of the invention. E, L or P-selectin transfected COS cells will adhere to a subset of compounds of the invention which can be resolved on TLC plates or adsorbed on PVC microtiter wells. Adhesion tests are preferably done under physiological conditions. Adhesion to these compounds may require calcium, but will not be inhibited by heparin, chondroitin sulfate, keratin sulfate, or yeast phospho-mannan (PPME). Monosaccharide composition, linkage analysis, and FAB mass spectrometry of the purified compounds will indicate that the ligands for E, L or P-selectin share common structural characteristics which generally relate to the moieties A and B and the position in which they are held.

Identification of Compounds Which Act as E, L and/or P-selectin Ligands Using Recombinantly Produced Receptor A complete cDNA for the E, L and/or P-selectin receptor was obtained by PCR starting with total RNA isolated from IL-1 stimulated human umbilical vein endothelium. The resulting cDNA was inserted into the CDM8 plasmid (see Aruffo et al., *Proc Natl Acad Sci USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for E, L and/or P-selectin (Bevilacqua et al., *Science*, (1989) 24:1160; Polte et al., *Nucleic Acids Res* (1990) 18:1083; Hession et al., *Proc Natl Acad Sci USA* (1990) 87:1673). These publications are incorporated herein by reference for their disclosure of E-selectin and genetic material coding for its production. The complete nucleotide sequence of the E-selectin cDNA and predicted amino acid sequence of the E-selectin protein are given in the above cited article by Bevilacqua et al., which DNA and amino acid sequences are incorporated herein by reference (see also published PCT patent application WO90/13300 which was published Nov. 15, 1990, which is incorporated herein by reference).

COS cells, expressing membrane-bound E, L and/or P-selectin, were metabolically radiolabeled with $^{32}PO_4$. These labeled cells can be used as probes in two assay systems to screen for recognition of the compounds of formula I or II. More specifically, compounds of formula I or II may be adsorbed to the bottoms of PVC microtiter wells or resolved on TLC plates. In either assay the compounds may be probed for their ability to support adhesion of E, L and/or P-selectin-transfected COS cells, untransfected COS cells, or COS cells transfected with a plasmid containing an irrelevant cDNA, under conditions of controlled detachment force (see Swank-Hill et al., *Anal Biochem* (1987) 183:27; and Blackburn et al., *J. Biol Chem.* (1986) 261:2873 each of which is incorporated herein by reference to disclose the details of such assaying methodology).

It has been indicated that $R^2$ may be a linker which may be any suitable and attachable moiety including a ceramide or a protein or peptide and is preferably a group with a reactive group thereon which allows it to covalently bind to a substrate or pharmaceutically active drug. In one embodiment of the invention the "linker" connects one or more ligands to a support base. The support base is then contacted with a sample to assay for the presence of a desired selectin in the sample.

The "linker" can be used to attach a pharmaceutically effective drug to the compound at the R position. The (Ligand-Linker-Drug) conjugate thus formed provides an effective drug delivery system for the linked drug. A method of attaching any moiety at the R position is shown in Reaction Scheme V.

NSAID or non-steroidal, anti-inflammatory drugs such as naproxen or ibuprofen which act as anti-inflammatory agents could be administered bound to the modified ligand and could be administered systemically in smaller amounts than usual while obtaining an equivalent effect or even greater anti-inflammatory effect at the site of inflammation. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation.

Method of Synthesis (General)

The compound of formulae I and II can be made using the general and specific synthesis schemes and examples described below. However, those skilled in the art will recognize variations thereof which are intended to be encompassed by the present invention. In general, the A and B moieties of formulae 1 and II are connected and held in a desired three-dimensional configuration. A simple reaction scheme for accomplishing such is shown below:

SCHEME 1

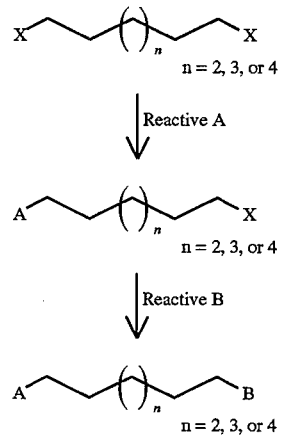

wherein each X is independently selected from the group consisting of —OH, —NH$_2$, —SH, and halogens such as Cl and Br; A and B are, respectively, a sialic acid and Fucose and their respective bioisosteres. A more specific version of reaction Scheme I is shown below:

REACTION SCHEME II

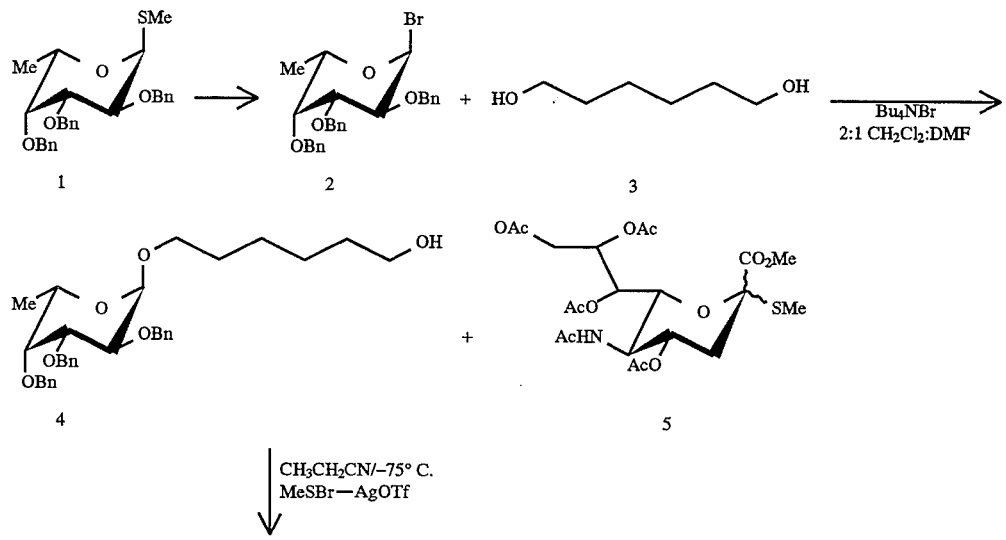

-continued
REACTION SCHEME II
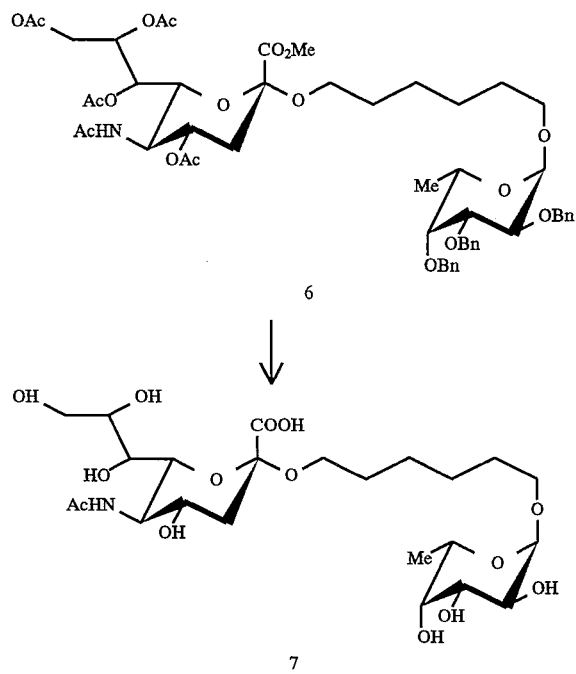
A reaction scheme wherein the fucose is attached is shown below.
REACTION SCHEME III
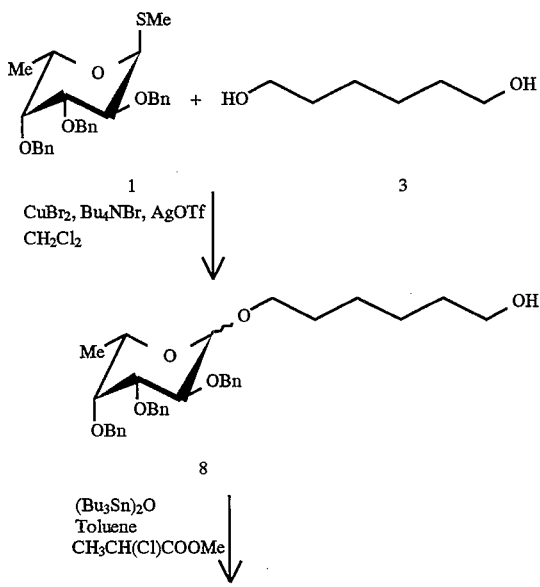
-continued
REACTION SCHEME III
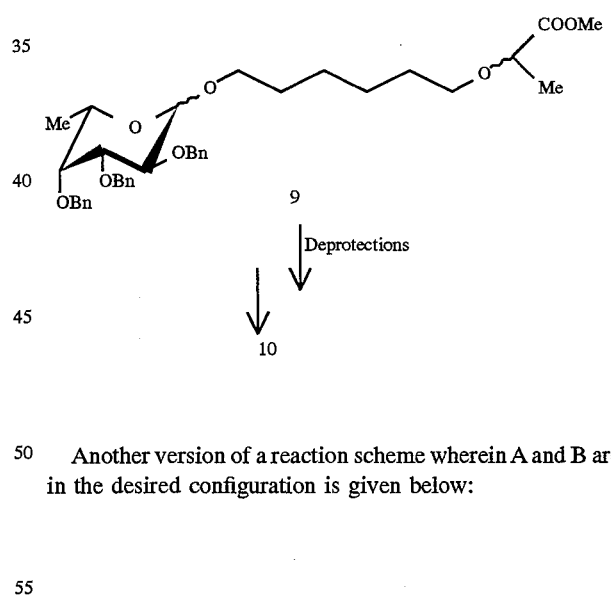
Another version of a reaction scheme wherein A and B are in the desired configuration is given below:

REACTION SCHEME IV
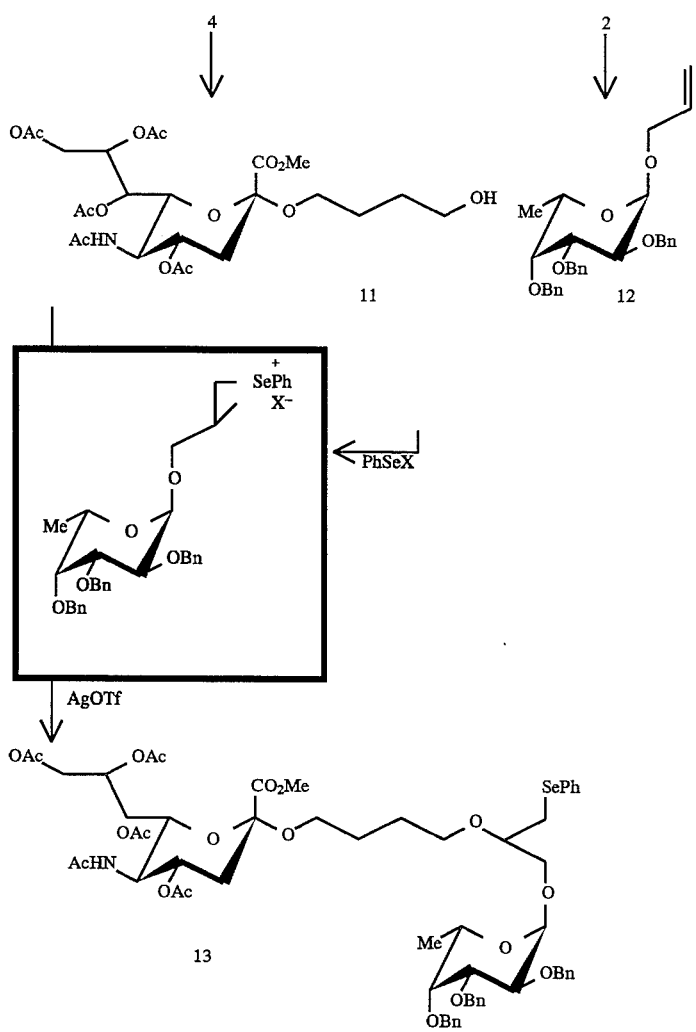
It is possible to alter a compound of formula I to obtain a compound which is labeled or attached to any other desired compound.
A general reaction scheme for obtaining such is as follows:
REACTION SCHEME V
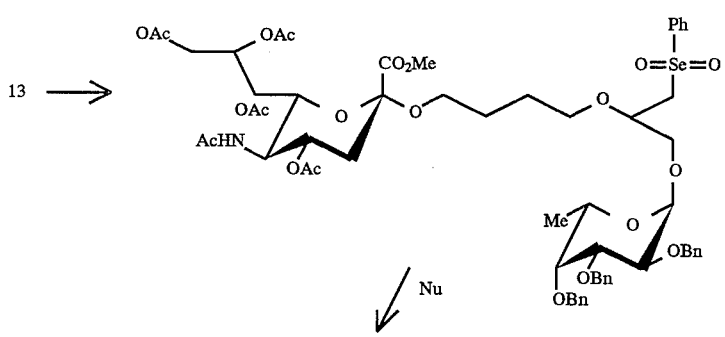

-continued
REACTION SCHEME V

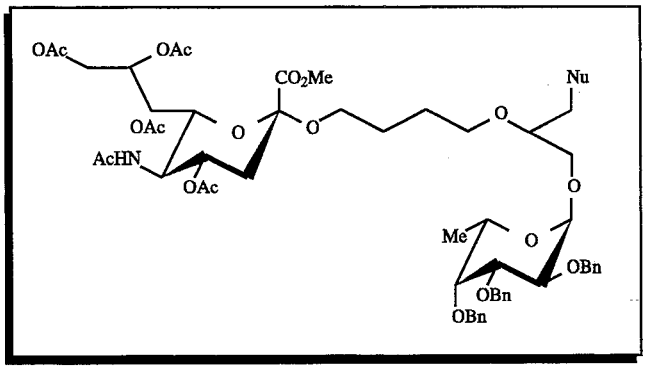

The compound shown above can then be reacted with a fluorescent probe, a multivalent compound, a ceramide, cholesterol or other lipid components, or a pharmaceutically active drug such as an anti-inflammatory drug.

Use and Administration

The compounds of the invention such as various ligands of structural formula I or II can be administered to a subject in need thereof to treat the subject by either prophylactically preventing inflammation or relieving it after it has begun. The ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the compounds directly in transdermal formulations with permeation enhancers such as DMSO. Other topical formulations can be administered to treat dermal inflammation.

A sufficient amount of compounds would be administered to bind to a substantial portion of the selectin expected to cause or actually causing the disease, for example, inflammation so that inflammation can either be prevented or ameliorated. Thus, "treating" as used herein shall mean preventing or ameliorating the appropriate disease. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

When determining the dose of compounds to be administered which block selectin receptors, it must be kept in mind that one may not wish to completely block all of the receptors. In order for a normal healing process to proceed, at least some of the white blood cells or neutrophils must be brought into the tissue in the areas where the wound, infection or disease state is occurring. The amount of the ligands administered as blocking agents must be adjusted carefully based on the particular needs of the patient while taking into consideration a variety of factors such as the type of disease that is being treated.

It is believed that the compounds of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the E-selectin receptors Within hours of the cells being damaged. The receptors are extended into the blood vessels where they adhere to glycolipid ligand molecules on the surface of white blood cells. Large numbers of white blood cells are quickly capture:l and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. Compounds of formula I or II can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g. Remington's Pharmaceutical Sciences, Mack Publishing Company, Easton, Pa., 17th edition, 1985. The composition or formulation to be administered will, in any event, contain a quantity of the compounds adequate to achieve the desired state in the subject being treated.

The various compounds of the present invention can be used by themselves or in combination with pharmaceutically acceptable excipient materials as described above. However, the compounds of the invention can be made as conjugates wherein the compounds are linked in some manner (e.g., via the $R^1$ moiety) to a label. By forming such conjugates, the compounds can act as biochemical delivery systems for the label so that a site of disease can be detected.

For instance, carbohydrates can be labelled by a variety of procedures, for example: esterification of hydroxyl bonds to form a structure capable of complexing directly with a radioisotope or nmr enhancer; reaction of the carbohydrate with amino diacetic acid (IDA) in organic solvent to form an N-linked glycoside derivative which would be capable of complexing with a radioisotope via the nitrogen and oxygen atoms of the IDA group; or coupling of the carbohydrate to amino acids which may be labelled directly (e.g. cysteine, tyrosine) or labelled via a bifunctional chelating agent (e.g., lysine).

Appropriate radioactive atoms would include, for example, technetium 99 m ($^{99\,m}Tc$), iodine-123 ($^{123}I$) or indium-111 ($^{111}In$) for scintigraphic studies, or for nuclear magnetic resonance (nmr) imaging (also known as magnetic resonance imaging, mri), a label such as gadolinium, manganese or iron, or a positron-emitting isotope such as iodine-124, fluorine-19, carbon-13, nitrogen-15 or oxygen-17.

The compounds of the invention may be prepared in a sterile, non-pyrogenic medium and injected into the bloodstream of a patient at a dose to be determined in the usual way by the physician or radiologist. After a sufficient period for a good balance to have been reached between (i) specificity of binding to activated endothelium compared to non-specific distribution and (ii) total amount of compound on activated endothelium, the compound is imaged in a conventional way, according to the nature of the label used.

The compounds of the invention could also be used as laboratory probes to test for the presence of a selectin receptor such as a receptor of E, L and/or P-selectin in a sample. Such probes are preferably labeled such as with a radioactive label. There are a number of known labels including radioactive labeled atoms, e.g. radioactive C, O, N, P, or S, fluorescent dyes and enzyme labels which can be attached to compounds of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

UTILITY

The invention compounds have considerable utility for the treatment of certain diseases, as set forth herein. However, this is not their only utility. Another utility is identification of particular chemical moieties that are responsible for, or contribute to ligand binding to the different selectins. Using the selectin binding assays described herein it is readily determined which chemical moieties that make up a selectin ligand contribute to selectin binding.

EXAMPLES

The following examples are provided so as to provide those of ordinary skill in the art with a complete disclosure and description of how to make compounds and compositions of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

It is important to note that the invention compounds described below have 4 to 12 atoms associated with the lactose core of the tetrasaccharides that separate sialic acid from fucose, or that separate analogues or derivatives of sialic acid from fucose and vice versa.

Example 1

1-O-(2,3,4-tri-O-benzyl-α-L-fucopyranosyl)-Hexane-6-ol (4)

Hexane-1,6-diol (3, 6 g. 25 mole) was dissolved in 2:1 1,2 dichloro-ethane-N,N-dimethyformamide (30 ml), Bu$_4$NBr (4.0 g,) was added and the mixture was stirred at room temperature (3h) under inert (argon) atmosphere. A solution of methyl 2,3,4-tri-O-benzyl-1-L-fucopyranosyl bromide (2) [prepared by the reaction of 2,3,4-tri-O-benzyl-thio-α-L-fucopyranoside (1, 1 g) with bromine (70 µl)] in dichloroethane (1 ml) was added into the reaction mixture. T.L.C. (5:1:0.5 Toluene-Acetone-MeOH) showed formation of product. Multiple elution on T.L.C. (6:1×1 and 8:1×2 Toluene-Ethyl acetate) indicated one major (RF=0.34) and one minor (RF=0.30) product. Filtration, evaporation and column chromatographic purification afforded the title compound 4 (major product) as a syrup (730 mg), $[\alpha]^{22}_D$ −44°, $[\alpha]^{22}_{436}$ −79° (c, 2.2 CHCl$_3$). $^1$H-NMR (CDCl$_3$): 7.5–7.2 (m, 15H, aromatic), 5.00–4.61 (m, 7H, 3 CH$_2$ Ph, H-Fucp), 4.78 (d, J 3.4 Hz, H-1 fuc1), 4.03 (dd, 1H, J 3.5 Hz, 10.1 Hz, H-2 Fucp), 3.93 (dd, 1H, J 2.75 Hz, 10.2 Hz, H-3 Fucp), 3.86 (bq, 1H, J 6 Hz, H-5 Fucp), 3.64 (bd, 1H, J 2.1 Hz, H-4 Fucp) 3.58 and 3.42 (2m, 2H —CH$_2$) and 1.1 (d, 3H, J 6.51 Hz, CH$_2$OH), 3.54 (t, 2H, J 6.6 Hz, —OCH$_2$—), 2.0 (bs, 1H, —OH), 1.62 and 1.52 (2m, 4H 2CH$_2$), 1.35 (m, 2CH$_2$) and 1.1 (d, 3H, J 6.51 Hz, CH$_3$ Fucp). $^{13}$C-NMR (CDCl$_3$): δ138.9, 138.5 (3 C-1 Ph), 97.3 (C-1), 79.3, 77.7, 76.43 (C-2), 66.07 (C-5), 7–4.7, 73.18, 73.15 (3 CH$_2$Ph), 67.99, 62.56 (2 OCH$_2$) 32.5, 29.3, 25.97, 25.48 (4 CH$_2$) and 16.6 (CH$_3$). Calcd. for C$_{33}$HA$_2$O$_6$, Exact Mass: 534.29. Found by f.a.b.-m.s.: 535.6 (M+1)+, 580.0 (M+NO$_2$)–, 687.8 (M+NBA)–.

Further elution afforded the mixture of α, and β fucosides (65 mg) followed by the pure β-anomer, (140 mg), [α]$^{22}_D$– 0.85, [α]$^{22}$436$^{–1.8}$ (c 1.77, CHCl$_3$); $^1$H-NMR (CDCL$_3$): δ4.3 (d, 1H, J 7.7 Hz, H-1), 3.8 (dd, 1H, J 7.7 Hz); 1.17 (d, 3H, J 6.4 Hz, CH$_3$) $^{13}$C-NMR (CDCL$_3$); δ103.8(C-1), 82.5, 79.4 (C-3), 76.2 (C-2), 70.2 (C-5, moved downfield), 75.1 (C-4, moved downfield), 74.5, 73.1, 69.6, 62.8, 32.6, 29.7, 25.9, 25.5 (6 CH$_2$), 16.86 (CH$_3$). Total yield 935 mg (81%).

Example 2

Methyl 5-Acetamido-4,7,8,9-tetra-O-acetyl-3,5-di-deoxy-2-O-[6-O-(2,3,4-tri-O-benzyl-α-L-fucopyranosyl)Hexyl-D-glycero-α-D-galacto-2-nonulopyranosonate(6)

Compound 4 (329 mg) and 5 (970 mg) were dissolved in dry propionitrile (5.0 ml), molecular sieve 4A° (1 g) was added and the mixture was stirred for 2 h at room temperature. Silver Triflate (1.1 g) was added and the septum sealed flask, containing the mixture was cooled to –73° C. A solution of methyl sulfenyl bromide (950 µl) in dichloroethane (989.9 mg/2.55 mL) was injected into the reaction mixture.

After 2 h, the reaction was terminated by the addition of a solution of Et$_3$N in CHCl$_3$ (1 mL in 5 ml), filtration, washing with water, drying (MgSO$_4$), filtration and evaporation of the organic layer afforded crude product mixture which was column chromatographically purified to afford the name compound 8 (178 mg, 30%) as a syrup [α]$_D$–240°; [α]$_{436}$–42.3° (c 1.55, CHCl$_3$). $^1$H-NMR (CDCl$_3$). δ7.4–72.5 (m, arom), 5.38 (m, H-8 Neu5Ac), 5.35–531 (2d, H-7 Neu5AC), 5.20 (d, NH), 5.00–4.63 (bd, 3 CH$_2$Ph), 4.77 (d, J 3.8 Hz, H-1Fuc), 4.31 (2dd, H-9a Neu5Ac), 4.02 (2dd, H-2 Fuc), 2.75 (dd, J 467 Hz, 12.82 Hz, H-3e Neu5AC), 1.56 [bm, 4H, (CH$_2$)$_2$], 1.31 [bm, 4H, (CH$_2$)$_2$], 1.10 (d, J 6.53 Hz, CH$_3$ Fuc). $^{13}$C-NMR (CDCl$_3$): δ170.019, 170.648, 170.257, 170.151, 170.060, 168.498 (6CO), 138–998, 138–725, 138–604 (3 Cl-Ph), 98.72 (C2, Neu5Ac), 97.38 (C-1 Fuc), 74.77, 73.25, 73.16, 67.98, 65.01, 62.34, (3-OCH$_2$Ph, 2-OCH$_2$—CH$_2$, C-9 Neu5Ac), 52.63 (OCH$_3$), 49.34 (C-5 Neu5Ac), 38.09 (C-3 Neu5Ac), 29.55, 29.36, 25.90, 25.71 (4CH$_2$—), 23.18 (NCOCH$_3$), 21.2, 20.86, 20.79 (1:2:1, OCOCH$_3$) and 16.65 (CH$_3$ Fuc).

Example 3

1-O-α-Neu5Ac-(6-O-α-L-Fucopyranosyl)-Hexane (7)

Compound 6 was deacetylated in methanol using sodium methoxide. After neutralization with cationic resin (IR120-H+) at ~0°–5° C., the solution was filtered and evaporated to give a syrup. The syrupy material was dissolved in 1:1 10% aqueous methonal-p-dioxane (5 ml) and reacted with 0.2M aqueous potassium hydroxide (1.5 ml) for 15 h at 0° C.—room temperature. The reaction mixture was neutralized with IR 120 (H+), filtered and evaporated to give a syrup (R$_f$=0.37, TLC in 2:1 CHCl$_3$-10% aq. MeOH). This material was dissolved in 10% aq. MeOH (5 ml) and hydrogenated at atmospheric pressure over 5% Pd-C (100 mg). TLC of the hydrogenated product showed only one product (R$_f$=0.06, 2:1 CHCl$_3$-10% aq. MeOH). The reaction mixture was filtered through Celite, concentrated, and the product was purified by chromatography from a biogel P2 column using water as the eluant. Appropriate fractions were pooled and lyophilized to afford pure 7. $^1$H-NMR data (D$_2$O-acetone): δ4.85 (d, J 3.85 Hz, 1H-fuc), 402 (q, 1H, H-5 fuc), 3.85–3.35 (ring protons and 2OCH$_2$), 2.7 (dd, J 4.64 Hz, H-3e Neu5Ac), 2.0(s, 3H, NHCOCH$_3$), 1.65–1.45 (m, 5H, H-3a Neu5Ac and 2 CH$_2$), 1.35 (bm, 4H, 2CH$_2$) and 1.18 (d, J 6.65 Hz, CH$_3$-Fuc). Molec. Formula, C$_{23}$H$_{41}$NO$_{14}$ (Mol. Wt., 555.58, Exact mass, 555.253). Found: 556.5 (M+1)+, 688.2 (M+Cs)+, 292.2 (2,3-dehydro Neu5Ac), 265.3 (M–Neu5Ac)+ and 554.2(M–1)–, 290.4 (Neu5Ac)–.

EXAMPLE 4

6-O-[(R,S)-1-Methoxycarbonyl-ethyl]-Hexanyl-2,3,4-Tri-O-benzyl-α-L-Fucopyranoside(9)

Compound 1 (2.9 g, 6.2 mmol) and 3 (37 g, 313.0 mmol) were transferred into 500 ml flask, dried under high vacuum (8 h), and dissolved in 6:1 dichloromethane-N,N-Dimethyformamide (350 ml). Molecular sieve 4A (5 g) was added and the solution was stirred (2 h), then cooled (0° C.) before the addition of CuBr$_2$ (2.33 g) and Bu$_4$NBr (3.7 g), into it. The dark reaction mixture was stirred at room temperature (3–4 h), filtered through Celite and the total filtrate was washed with saturated NaHCO$_3$, saturated NaCl and water. The organic layer was dried (MgSO$_4$), filtered and evaporated to give a syrup. Column chromatography from dry silica gel column (400 g), using 10:1 (300 ml), 40:1 (1.5 L) and 20:1 toluene-acetone afforded the pure product (8) as a syrup (1 g.). Molecular formula C$_{33}$H$_{42}$O$_6$ (Mol. wt. 534.70). Found: 535.6 (M+1)+, 417.4 (M–117)+ and 580.0 (M+NO$_2$)–, 687.8 (M+NBA)–. $^1$H-and $^{13}$C-NMR indicated it to be a mixture of α and β-L-fucopyranosides.

Compound 8 (0.97 g) was dispersed in toluene (50 ml) in a 100 ml flask equipped with Dean-Stark assembly. Toluene (15 ml) was distilled off followed by the addition of (Bu$_3$Sn)$_2$O (1.52 ml) into the reaction mixture. More toluene (20 ml) was distilled off and the resulting solution was refluxed (2–3 h). All the toluene was evaporated off on a rotatory evaporator using a short neck distillation assembly fitted with a stop cock. The evacuated flask containing the stannylated material was shut off using the stop cock and removed from the rotavap. Argon was introduced into the flask followed by methyl 2-chloropropionate (1.5 ml). The content was stirred and heated (95°–100° C.) under an argon atmosphere for 12 h. The mixture was cooled with crushed ice followed by the introduction of dichloromethane (15 ml) into the flask. The total content was transferred into a separatory funnel, the organic layer was washed with water, separated and dried (MgSO$_4$). Filtration and evaporation of the dichloromethane afforded crude product which was transferred on dry packed silica gel (150 g ) column and eluted with toluene (120 ml) followed by 60:1 (200 ml) and 80:1 toluene-acetone. The anomeric mixture of products (9) was isolated as a syrup. $^{13}$C-NMR (CDCl$_3$-TMS): δ170.14 (CO), 103.79 (C1 β-L-Fucp, 97.45 (C1 α-L-Fucp; α:β-5.5:1), 52.8, 52.56 (OCH$_3$), 21.49 (Lactyl CH$_3$), 16.6, 16.8 (CH$_3$ of α- and β-L-Fucp).

EXAMPLE 5

1-O-(α-β-L-Fucopyranosyl)-6-O-[(R,S)-1-Carboxyethyl]-Hexane (10)

Syrupy 9 was dissolved in 10% aqueous methanol and hydrogenated (2 days) in the presence of 10% Pd-C under atmospheric pressure. Completion of the reaction was determined by TLC (5:1:0.2 toluene-acetone-10% aq. MeOH). The reaction mixture was filtered through Celite and the clear filtrate was evaporated to dryness to yield the crude product 10. $^1$H-NMR of 10 indicated complete absence of the aromatic signals.

Figure 3:
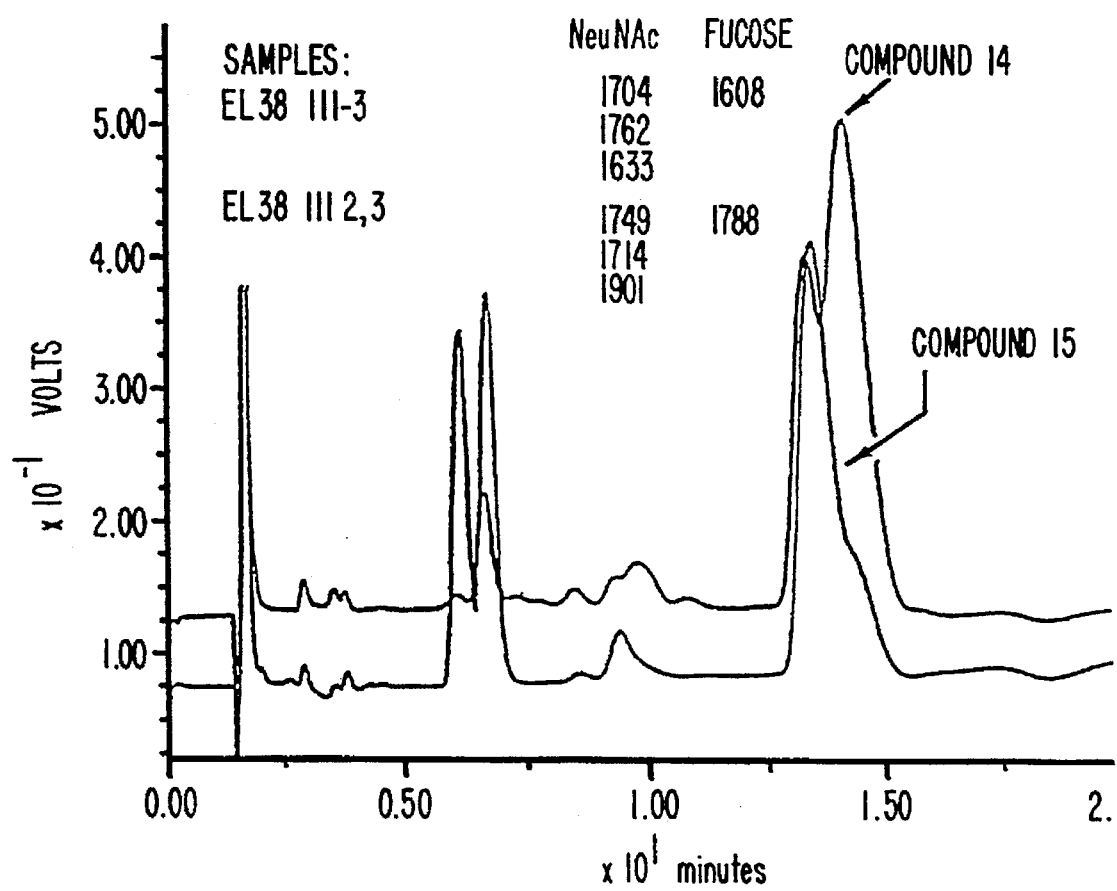
FIG. 3 is a graph showing the column chromatograph of two specific compounds; 14 and 15.

Compound 10 was dissolved in 1:1 p-dioxane-MeOH (2.5 ml), 10% aq. MeOH (3.0 ml) was added followed by the addition of 0.2M aq. KOH (1.5 ml) at 0°–5° C. Reaction was then continued for 8–10 h at room temperature. TLC (every hour in 5:1:1 toluene-acetone-10% aq. MeOH) indicated conversion into product with lower $R_f$. The reaction mixture was neutralized with IR 120 (H+), filtered and evaporated. The syrup was charged on dry packed silica gel column and eluted with 5:1:1 toluene-acetone-10% aq. MeOH. The GC-MS of the pure product ($R_f$=0.17), as its permethylated derivative showed one major and one minor component (due to the α and β-L-Fucopyranose), having the same fragmentation pattern with major m/e at 189 (2,3,4-Tri-O-methyl-L-Fucose)+, 157 [m/e 189-32(OCH$_3$)], 115 and 88 [i.e. total 203 due to {O-Hexyl-O—CH—(COOCH$_3$)(CH$_3$)}] (FIG. 3).

EXAMPLE 6

Synthesis of O-Hexamethylene linked α,β-NeuNAc and α,β-L-Fucopyranose (14 and 15)

Compound 8 (203.6 mg) and donor 5 (597 mg) were dissolved in acetonitrile (7.0 ml) and stirred (1 h) in the presence of molecular sieve 4A (2 g). Silver triflate (764 mg) was added and the mixture was cooled (–30° C.), before the addition of a solution of methyl sulfenyl bromide (355 μl of a stock solution containing 989.9 mg/2.55 ml). At the end of the reaction (2–3 h), the reaction was worked up in the usual manner and the crude product was charged on a silica gel (350 g) column and eluted successively with 5:1:0.1 (180 ml) and 7:1:0.1 (Toluene-Acetone-MeOH). The product was isolated as mixtures in two major fractions (76–83) and (84–110) respectively. $^{13}$C NMR of both fractions showed: δ171.0, 170.65, 170.25, 170.18, 170.15, 170.056 and 168.5 (CO), 138.99–138.57 (6 C-1 Ph), 103.79 (β-fuc C-1), 98.71 (C-2 Neu4Ac), 97.38 (α-fuc C-1), 52.63 (OCH$_3$), 49.36 (C-5 Neu5Ac), 38–08 (C-3 Neu5Ac), 29.7–29.3 (3CH$_2$), 25.9–25.7 (3CH$_2$), 23.2 (NHCOCH$_3$), 21.1–20.8 (OCOCH$_3$) and 16.88, 16.67 (CH$_3$ of α,β-L-Fuc).

NMR indicated that the first product mixture contained larger proportions of α-fuc and β-NeuNAc.
Deprotection Each pool of fractions were deprotected separately. Deacetylation was carried out in methanol (dry) using catalytic sodium methoxide. After neutralization (IR 120H+), filtration and evaporation, the syrups were dissolved in 2:1 MeOH—P-Dioxane (3 ml) and saponified by the addition of 0.2M aqueous KOH (1.5 ml) to give products ($R_f$=0.35 and 0.33), T.L.C. solvent (2:1 CHCl$_3$-10% aqueous MeOH).

Expected molecular formula: C$_{44}$H$_{59}$NO (M. wt: 825.96; Exact Mass: 825.39). Found: 848.5 (M+Na)+ and 824.6 (M–1)–.

The syrupy products were dissolved in 10% aqueous MeOH and hydrogenated over 10% Pd-C at 1 atmosphere until T.L.C. (2:1 CHCl$_3$-10% aqueous MeOH) indicated absence of the starting compounds and appearance of new products ($R_f$=0.17), filtration, evaporation and lyophilizations afforded two mixtures (14 and 15). Expected molecular formula: C$_{23}$H$_{41}$NO$_{14}$ (M. wt. 555.552, Exact mass: 555.253). Found: 556.5 (M+1)+, 578.5 (M+Na)+, 292.2 (2,3-enesialic acid+1)+, 265.3 (M–291)+ and 554.2 (M–1)–.

Figure 4:
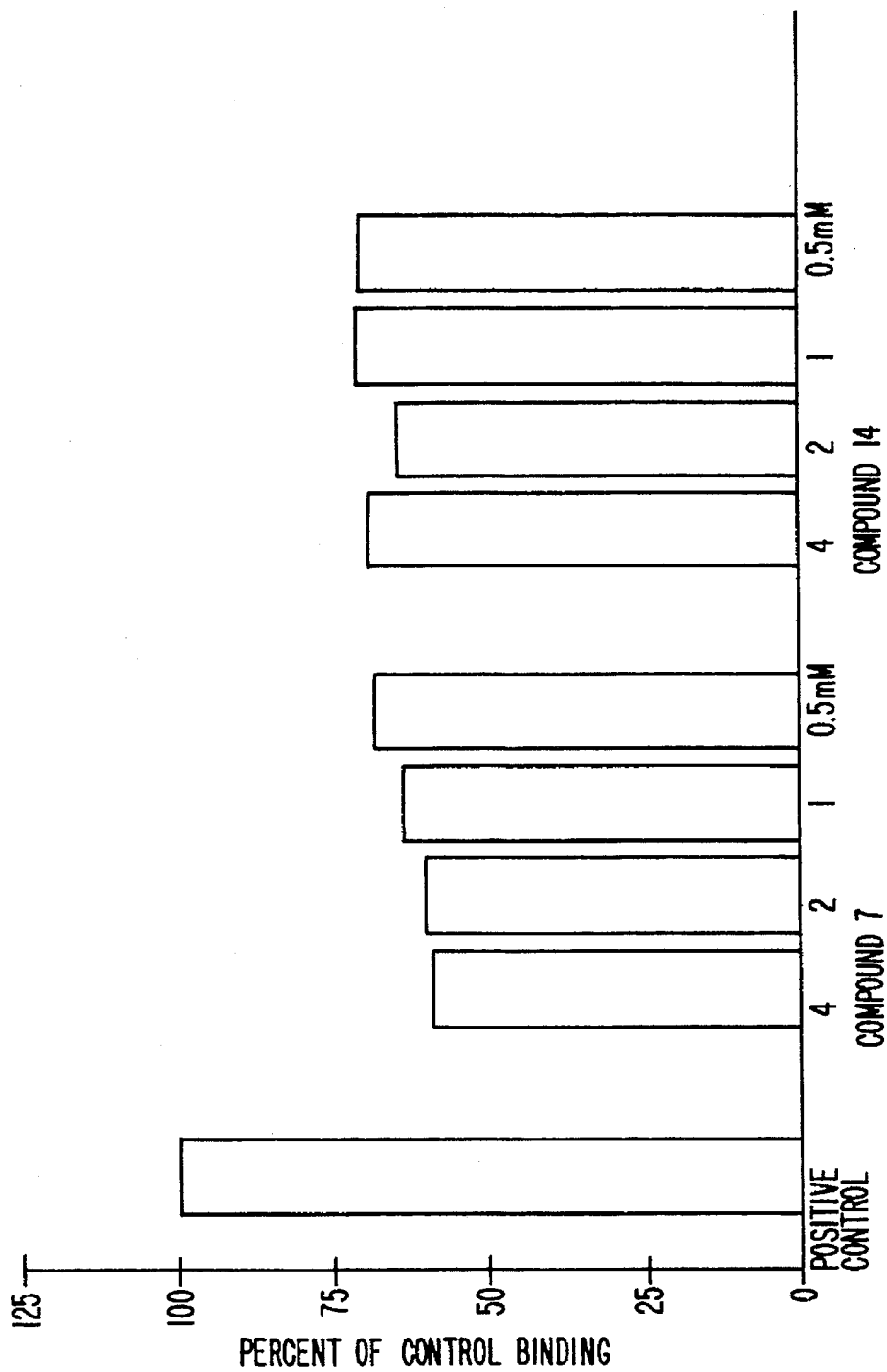
FIG. 4 is a graph showing the results of Elisa assays carried out to determine the ability of two different compounds to block the binding of 2,3,sialyl-Le$^x$ to E-selectin IgG chimera. The compounds tested were 7 and 14. The compounds were tested at several concentrations as shown in the figure, and the results expressed as the per cent of control binding.

Analysis and Testing Analysis and testing of two specific products referred to as 14 and 15 is described below. The structure of each of these compounds was shown above. Comparison of the T.L.C. of α-Neuraminidase treated 14 and 15 showed that both contained α-linked sialic acid as the major component. However, NMR had indicated that the first of the two mixtures contained larger proportion of α-L-fucose. These samples were individually analyzed by Dionex (Carbopak DA-1 column with isocratic running 0.1M NaOH) and were found to contain equal proportions of Fucose and Neu5Ac. The elution profile indicated the presence of four distinct signals for both 14 and 15, (FIG. 4). Based on the NMR information and T.L.C. data after neuraminidase treatment, the major signals, eluting at a slower rate, were designated to compounds having α-linked sialic acid. The faster eluted minor components contained β-linked L-fucoside. Pool 2 (14) contained higher proportions of β-L-fucopyranoside (O-linked through hexamethylene to a O-α-sialic acid).

EXAMPLE 7

Synthesis of a Novel β-Galactopyranoside (16)

Methyl 2,3-di-O-benzoyl-4,6-O-benzylidene-1-thio-β-D-galactopyranoside (1.5 g) and methyl-(2R,3R)-L-tartarate (5.8 g) were dissolved in dichloromethane (12 ml) containing molecular sieve 4A (4 g). After stirring for 1 h, silver triflate (1.2 g) was added followed by a solution of methyl sulfenyl bromide in dichloroethane (1.2 ml of 0.989 g/2.55 ml). TLC (toluene-acetone 10:1) indicated complete absence of the initial reactants and the formation of two products. Neutralization of the reaction mixture with Et$_3$N followed by filteration and aqueous work up afforded a syrupy product which was purified by silica gel chromatography (toluene-acetone 8:1). The α-galactoside eluted first (800 mg, 42%), $[α]_D$+191° (c 2, CHCl$_3$), followed by the pure β-galactoside 16 (880 mg, 47%), $[α]_D$+112° (c. 1.5, CHCl$_3$), m.p. 169°–170° C. 1H-NMR (CDCl$_3$-TMS): 8.0–7.3 (15H, aromatic), 5.85 (dd, J 10 Hz, 1H, H-2), 5.48 (s, 1H, PhCH), 5.35 (dd, J 10 Hz, 3.5 Hz, 1H, H-3), 5.0 (d, J 8.1 Hz, 1H, H-1), 4.72 (d, J 2.8 Hz, 1H, H-2'), 4.56 (m, 2H, H-3', 4), 4.3–4.2 (2 dd, H-6a, 6b), 3.69 (s, 3H, OCH3), 3.66 (bs, 1H, H-5), 3.52 (s, OCH3), 3.38 (d, J 8.8 Hz, OH).

EXAMPLE 8

Synthesis of Methyl-L(+)-(2R, 3R)-2-O-(2,3,4-tri-O-benzyl-α-L-fucopyranosyl)-tartarate(17)

Thiofucoside (1) and methyl-L-(2R, 3R)-tartarate were reacted in N,N-DMF-dichloroethane under the conditions described for the synthesis of compound 8 to afford a mixture of α and β fucosides, the β fucoside 17 was isolated as the major product by silica gel column chromatography (toluene-acetone 40:1). The syrupy material had $[α]_D$; molecular formula C$_{33}$H$_{38}$O$_{10}$ (594). Found: 617.1 (M+Na)+ and 595.1 (M+H)+.

EXAMPLE 9

Synthesis of Methyl-D(–)-(2S,3S)-2-O-(2,3,4-tri-O-benzyl-β-L-fucopyranosyl)-tartarate (18)

Thiofucoside (1) and methyl-D(–)-(2R,3R)-tartarate were reacted in N,N-DMF-dichloroethane under the conditions described for the synthesis of compound 8 to afford a mixture of α and β fucosides, the β fucoside (18) was isolated as the major product by silica gel column chroma-

29 tography (toluene-acetone 40:1). The syrupy material had [α]$_D$; molecular formula C$_{33}$H$_{38}$O$_{10}$ (594). Found: 617.1 (M+Na)+ and 595.1 (M+H)+.

EXAMPLE 10

Synthesis of Methyl L(+)-(2R,3R)-2-O-(2,3,4-tri-O-benzoyl-6-O-benzyl-β-D-galactopyranosyl)-3-O-(2,3,4-tri-O-benzyl-α-L-fucopyranosyl)-tartarate (19)

Compound 17 (1.2 g) was dissolved in dichloroethane (10 ml) and stirred (1–2 h) at room temperature under nitrogen atmosphere in the presence of molecular sieve 4A (3 g). Silver triflate (0.75 g) and 1,1,3,3-tetramethylurea (0.26 ml) were added, cooled to −15° C. and a solution of 1-bromo-2,3,4-tri-O-benzyl-6-O-benzoyl-D-galactopyranoside, prepared from the corresponding methyl-1-thio-precursor (1.48 g), was added. After the usual work up, chromatographic purification afforded pure 19 as a syrup (270 mg), [α]$_D$+21° (c 0.9, CHCl$_3$). $^1$H-NMR (CDCl$_3$-TMS): 5.92 (bd, J 3.2 Hz, 1H, H-4 gal), 5.65 (t, J 10 Hz, 1H, H-2 gal), 5.47 (dd, J 3.3 Hz, 10.3 Hz, 1H, H-3 gal), 1.05 (d, 3H, CH$_3$ of fucose); $^{13}$C-NMR: 168.84, 168.80, 168.55, 165.43, 165.39, (CO), 99.88, 97.10 (C-1 of gal and fuc), 74.71, 73.64, 73.21, 72.36, 67.69 (5 CH$_2$), 52.22, 52.13 (2OCH$_3$), 16.47 (CH$_3$ of fucose).

EXAMPLE 11

Synthesis of 1-O-(2,3,4-tri-O-benzoyl-6-O-benzyl-β-D-galactopyranosyl)-3-O-(2,3,4-tri-O-benzyl-α-L-fucopyranosyl)-propan-2-one A solution of 1-bromo-2,3,4-tri-O-benzoyl-6-O-benzyl-β-D-galactopyranoside in dichloroethane prepared from the corresponding methyl-1-thiogalactoside precursor (4.7 g) was added into a stirred mixture containing solketal (3.0 ml), molecular sieve 4A (3.0 g), silver triflate (2.8 g), and 1,1,3,3-tetramethylurea (0.75 ml) in dichloroethane (7 ml) at −15° C. TLC (20:1 toluene-acetone) after 2 h indicated complete conversion into one product. After the usual work up and recovery of the product, the crude material was treated with 80% aqueous acetic acid at 60° C. (4 h) to give 1-O-substituted propane syn-2,3-diol (20).

Into a solution of 20 (3.0 g) in 2:1 dichloroethane-N,N-DMF (20 ml) containing Bu$_4$NBr (17 g) was added a solution of 2 (3.0 g), and the mixture was stirred at room temperature (14 h). Chloroform (20 ml) was added and the reaction mixture was filtered, washed with water, dried (MgSO$_4$), filtered and evaporated to give the crude product. Column chromatography afforded the pure 1-O-(2,3,4-tri-O-benzoyl-6-O-benzyl-β-D-galactopyranosyl)-3-O-(2,3,4-tri-O-benzyl-α-L-fucopyranosyl)-propan-(R,S)-2-ol (21) as a syrup.

Acetic anhydride (4.0 ml) was added into a solution of 21 (4.6 g) in dimethyl sulfoxide (25 ml) and the reaction mixture was stirred at room temperature under an atmosphere of nitrogen for 12 h. TLC (10:1 toluene-acetone) indicated conversion of the starting compound (R$_f$=0.18) into one product (R$_f$=0.29). The reaction mixture was lyophilized and quickly eluted through a silica gel column to afford compound 22 (4.05 g, 88%), [α]$_D$+25° (c 1.2, CHCl$_3$). $^{13}$C-NMR (CDCl$_3$-TMS): 204.1 (CH$_2$COCH$_2$), 165.46, 165.39, 165.36 (CO of Bz), 101.04 (C-1 Gal), 97.62 (C-1 of Fuc), 74.84, 73.56, 73.34, 72.99, 72.23, 70.14, 67.56 (7 CH$_2$), 16.5 (CH$_3$ of Fuc) and 78.93, 77.72, 75.97, 72.86, 71.54, 69.57, 68.16, 66.90. Molec. formula C$_{64}$H$_{62}$O$_{15}$ (1071.12): Calcd. exact mass 1070.4. Found: 1093.1 (M+Na)+.

30

EXAMPLE 12

Synthesis of [O-(α-L-fucopyranosyl)-ethyl]3-O-(α-Neu5Ac)-β-D-galactopyranoside (28)

Ethylene glycol (5.0 ml) was dissolved in acetonitrile (25.0 ml) containing molecular sieves 4A (5.0 g) and stirred at room temperature for 1.5 h. Silver triflate (870 mg) was added into the flask followed by a freshly prepared solution of methyl sulfenyl bromide (MSB) in dichloroethane (DCE) (500 µl of 0.99 g/2.0 ml). Immediately after the addition of MSB, a solution of the donor 23 (methyl 4,6-O-benzylidene-2,3-di-O-benzoyl-1-thio-β-D-galactopyranoside, 495 mg in 1.0 ml) was added dropwise (20 min) into the reaction flask with vigorous stirring at room temperature. Additional amount of MSB (400 µl) and 23 (495 mg in 1.0 ml) were added and the reaction allowed to go to completion. TLC (15:1:1 toluene-acetone-methanol) indicated one product (Rf=0.22) which was isolated column chromatographically, after the usual work up, to give 2-hydroxy ethyl 4,6-O-benzylidene-2,3-di-O-benzoyl-b-D-galactopyranoside (24, 950 mg, 94%), m.p. 191°–192° C. (CH$_2$Cl$_2$-Hexane), [α]$_D$+ 139° (c 1.2, CHCl$_3$). $^1$H-NMR (CDCl$_3$-TMS): 5.87 (dd, J 8.0 Hz, 1H, H-2), 5.54 (s, 1H, PhCH), 5.39 (dd, J 3.5 Hz, 10.45 Hz, 1, H-3), 4.80 (d, J 8.0 Hz, 1, H-1), 4.51 (bd, J 3.0 Hz, 1, H-4), 2.62 (bs, 1, OH). $^{13}$C-NMR: 166.17, 165.45 (2CO), 101.65, 100.79 (C-1, PhCH), 72.01, 68.87, 61.64 (3CH$_2$) and 73.47, 72.51, 69.20, 66.59. Molecular formula C$_{29}$H$_{28}$O$_9$ (520.505), Calcd. exact mass: 520.173. Found: 521.5 (M+H)+, 543.4 (M+Na)+ and 673.6 (M+NBA)−.

The galactoside acceptor (24, 940 mg) and the thiofucoside donor (1, 1.1 g) were dissolved in 5:1 DCE:DMF (10 ml) and the solution stirred (1 h) under nitrogen over molecular sieve 4A (1.75 g). Into this solution was added cupric bromide (0.75 g) and Bu$_4$NBr (1.30 g). TLC (10:1 toluene-acetone) after 6 h indicated complete conversion into one product (Rf=0.34). After the usual work up the syrupy product was eluted from a dry silica gel column (150 g ) with 10:1 (200 ml) and 20:1 toluene-acetone to give a mixture containing both α and β linked fucoside (25, 0.55 g, α:β2.2:1 by NMR) and pure α-L-fucoside as a syrup (0.72 g), [α]$_D$+31° (c 2.3, CHCl3). 13C-NMR (CDCl3-TMS): 166.08, 165.07 (2CO), 100.58, 100.46 (C-1, PhCH), 97.82 (C-1 Fuc), 74.76, 73.24, 72.78, 68.90, 68.03, 67.03 (6CH2), 16.48 (CH3 of Fuc) and 79.34, 77.79, 76.17, 73.49, 72.69, 69.15, 66.31, 66.16. Elemental Anal. Calc. for C$_{56}$H$_{56}$O$_{13}$.MeOH (969.036): C, 69.41%; H, 5.82%. Found: C, 69.99%; H, 5.72%.

Debenzoylation of 25 was carried out in methanol with sodium methoxide to afford the dihydroxy compound 26, m.p. 140°–143° C., [α]$_D$−40° (c 1.3, CHCl$_3$). $^{13}$C-NMR (CDCl$_3$-TMS): 138.86, 138.54, 138.25, 137.58 (C1-Ph), 103.52 (C-1 gal), 101.22 (PhCH); 98.11 (C-1 fuc), 16.61 (CH$_3$-fuc). Elemental Anal. Calc. for C$_{42}$H$_{48}$O$_{11}$ (728.793): C, 69.20%; H, 6.64%. Found: C, 68.11 %,;H, 6.64%.

The dihydroxy acceptor (26, 163 mg) and thiosialoside donor (5, 591mg) were dissolved in acetonitrile (7.0 ml) and stirred (2 h) in the presence of molecular sieves 4A (2.4 g). Silver triflate (614 mg) was added, stirred to dissolve and the reaction mixture was cooled (−43° C.). MSB (348 µl) was added and the reaction continued overnight (12 h) at the end of which the reaction was terminated by the addition of Et$_3$N (1.0 ml). Filteration and washing the residue with chloroform (10 ml) was followed by washing of the filtrate with aq. NaHCO$_3$ and water. Drying (MgSO$_4$) and evaporation of the filtrate afforded the crude product from which the desired sialylated compound 27 was isolated by column chromatography as a syrup (78 mg). Molecular formula $C_{62}H_{75}NO_{23}$ (1202.28): Exact Mass Calcd. 1201.473. Found: 1224.6 (M+Na)+, 1202.9 (M+H)+, 1247.2 (M+$NO_2$)−, 1354.5 (M+NBA)−.

Hydrogenation followed by base hydrolysis afforded the title compound 28, molec. formula $C_{25}H_{43}NO_{19}$ (661.62). Exact Mass Calcd. 661.24. Found: 662.8 (M+H)+, 660.1 (M−H)−.

EXAMPLE 13

Synthesis of 1-O-(3-O-α-carboxy ethyl-β-D-galactopyranosyl)-2-O-(α-L-fucopyranosyl)-3-O-(n-propyl)-propane(32)

Compound 20 (3.1 g) was activated with dibutyl tin oxide (2.46 g) in toluene and treated with allyl bromide (0.8 ml) in the presence of tetrabutyl ammonium bromide (2.16 g). After 12 h, tlc (15:1:0.1 toluene-acetone-methanol) indicated the formation of one major product ($R_f$=0.32). The reaction mixture was evaporated to a syrup, charged on a dry silica gel column (140 g) and eluted with toluene (140 ml), 10:1:0.1 toluene-acetone-methanol (100 ml) and 20:1:0.1 toluene-acetone-methanol successively to give 1-O-(2,3,4-tri-O-benzoyl-6-O-benzyl-β-D-galactopyranosyl)-3-O-allyl-propan-2-ol (29, 2.02 g).

Fucosylation of 29 (2.0 g) was carried out in 5:1 dichloroethane:DMF (12 ml) using the fucosyl donor (1, 3.0 g) in the presence of $CuBr_2$ (1.72 g), $Bu_4NBr$ (3.83 g) and molecular sieve 4A (2.8 g) at room temperature. After the usual work up, the product was isolated from the crude mixture by careful column chromatography to give 1-O-(2,3,4-tri-O-benzoyl-6-O-benzyl-β-D-galactopyranosyl)-2-O-(2,3,4-tri-O-benzyl-α-L-fucopyranosyl)-3-O-allyl-propane (30, 1.0 g). Compound 30 was dissolved in methanol (10 ml) and deacylated with NaOMe (50 mg) to give 1-O-(6-O-benzyl-b-D-galacto-pyranosyl)-2-O-(2,3,4-tri-O-benzyl-α-L-fucopyranosyl)-3-O-allyl-propane (31, 400 mg). Molecular formula $C_{46}H_{56}O_{12}$ (molec. wt. 800.89); found 823.4 (M+Na)+.

Compound 31 (370 mg) was activated with dibutyl tin oxide (215 mg) in methanol (50 ml) and then treated with ethyl-2-bromopropionate (1.4 ml) in the presence of $Bu_4NBr$ (1.58 g). The product, 1-O-allyl-2-O-(2,3,4-tri-O-benzyl-α-L-fucopyranosyl)-3-O-[3-O-(2-O-2-ethoxy-carbonyl ethyl)-6-O-benzyl-β-D-galactopyranosyl]-propane, was isolated chromatographically and subjected to hydrogenation (10% Pd-C) at ambient pressure followed by hydrolysis in 0.2% aq. KOH. The deprotected material was neutralized with IR 120 (H+) filtered and lyophilized to give the title compound 32 (22.7 mg). Molecular formula $C_{21}H_{38}O_{14}$ (514.5). Found: 513.2 (M−H)−.

EXAMPLE 14

Synthesis of 3-O-sulfogalactoside containing product (35)

A methanolic solution of compound 30 is treated with thioethanol-2-amine in the presence of UV light to afford the chain extended compound 33. The amino group is protected with Z (Cbz or other) and the corresponding sulfone derivative (34), obtained by oxidation with p-methoxy perbenzoic acid, is deacylated with NaOMe in methanol. The trihydroxy galactosyl intermediate is selectively sulfated at the C-3 (of galactose) and deprotected in the usual manner, after forming the corresponding sodium salt, to afford the title compound 35. The product is eluted through a biogel-P2 column and lyophilized.

EXAMPLE 15

Synthesis of Glycerides

A 10:1 acetone-water solution of compound 30 is treated with $OsO_4$ in the presence of N-methyl morpholine N-oxide to afford the dihydroxy compound 36. Compound 36 is treated with 2,2-dimethoxypropane in the presence of camphor sulfonic acid (catalytic amount) to give 1-O-(2,3,4-tri-O-benzoyl-6-O-benzyl-β-D-galactopyranosyl)- 2-O-(2,3,4-tri-O-benzyl-α-L-fucopyranosyl)-3-O-(1,2-O-isopropylidene-propyl)-propane (37).

Sialosyl Diglyceride Derivative: Debenzoylation of 37 is followed by reaction of the resulting trihydroxy derivative with thiosialoside donor (5) in the presence of N-iodosuccinimide and methyl triflate in propionitrile at −70° C., to give 1-O-[3-O-(benzyl 5-acetamido-4,7,8,9-tetra-O-benzyl-5-deoxy-D-glycero-2-nonul-D-galactopyranosonate)-6-O-benzyl-β-D-galactopyranosyl]-2-O-(2,3,4-tri-O-benzyl-α-L-fucopyranosyl)-3-O-(1,2-O-isopropylidene-propyl)-propane (38a). Mild acid hydrolysis releases the isopropylidene ring and treatment with pentafluorophenyl active ester of the fatty acids gives the fatty acid esters of the glycerol as the major product. Hydrogenation and usual purification by chromatography gives the deprotected diglyceride (39a).

Sulfo Diglyceride Derivative: Selective sulfation of the debenzoylated product of 37 using stoichiometric quantities of the pyridine-$SO_3$ reagent gives 1-O-[3-O-sulfo-6-O-benzyl-β-D-galactopyranosyl]-2-O-(2,3,4-tri-O-benzyl-α-L-fucopyranosyl)-3-O-(1,2-O-isopropylidene-propyl)-propane (38b). Mild acid hydrolysis is followed by sodium ion exchange in order to retain the sodium counterion of the sulfate. Treatment with pentafluorophenyl active ester of the fatty acids gives the fatty acid esters of the glycerol as the major product. Hydrogenation and usual purification by chromatography gives the deprotected sulfo diglyceride (39b).

EXAMPLE 16

Synthesis of Pseudodisaccharide Containing Peptides

Solid support synthesis: 2,3,4,6-Tetra-O-acetyl-D-galactopyranosyl donor is reacted with solketal in the presence of a suitable activator and the resulting galactoside is hydrolyzed with 80% aqueous acetic acid at 60° C. to give a dihydroxy compound 40. Compound 40 is activated with dibutyl tin oxide (1.3 molar) in toluene and treated with benzyl bromoacetate (4.0 molar) in the presence of $Bu_4NBr$ (4.1 molar). At the end of the reaction, the reaction mixture is evaporated to a syrup, charged on a dry silica gel column, and eluted with toluene (140 ml), 10:1:0.1 toluene-acetone-methanol (100 ml) and 20:1:0.1 toluene-acetone-methanol successively to give 1-O-(2,3,4,6-tetra-O-acetyl-β-D-galactopyranosyl)-3-O-benzyloxy carbonyl methyl-propan-2-ol (41). Fucosylation of 41 is carried out in 5:1 DCE-DMF (12 ml) using the fucosyl donor (1) in the presence of $CuBr_2$ (1.5 molar), $Bu_4NBr$ (1.6 molar) and molecular sieve 4A at room temperature. After the usual work up, the product is isolated from the crude mixture by careful column chromatography to give 1-O-(2,3,4,6-tetra O-acetyl-β-D-galactopyranosyl)-2-O-(2,3,4-tri-O-benzyl-α-L-fucopyranosyl)-3-O-benzyloxy carbonyl methyl-propane (42). Hydrogenation followed by acetylation gives the peracylated intermediate (43), the free carboxyl function of 43 is activated to give the corresponding pentafluorophenyl ester (44). The ester is reacted with $N^2$-carbobenzyloxy-L-lysine to give the target compound ready for incorporation into a growing, predesigned peptide chain.

Solution phase synthesis: The ester 44 can also be reacted with a peptidic backbone containing free amino functions placed at predetermined distances.

EXAMPLE 17

Preparation Of 1-Deoxy-1-α-Iodoethyl-2,3,4-Tri-O-Acetyl-L-Fucose (48)

A solution of tetraacetylated L-fucose (9.0 g, 27.1 mmole) in acetonitrile (100 ml) was stirred with one teaspoon of powdered molecular sieves (4 A°) for 30 minutes. This solution was mixed with allyltrimethylsilane (17.6 ml) followed by borontrifluoroetherate (17.6 ml) solution in one portion. This reaction mixture was stirred at room temperature for three days. Most of volatiles were removed in vacco and diluted with a 1:1 mixture of saturated sodium bicarbonate and brine solutions (100 ml). This solution was extracted with ethyl acetate. (2×200 ml)and the combined organic extracts were washed with saturated sodium bicarbonate and brine solutions, dried over sodium sulfate, filtered and concentrated. The crude material was purified on a silica gel column (hexane:ethyl acetate, 3:1) to provide allylfucose (45, 7.97 9, 94%).

A solution of 45 (5.1 g, 16.3 mmole) in a mixture of dichloromethane (80 ml) and methanol (20 ml) at −78° C. was bubbled with ozone until the blue color persisted. Excess ozone was removed by passing oxygen through the solution. This solution was mixed with dimethylsulfide (10 ml) and stirred at −78° C. to room temperature overnight. All the volatiles were removed in vacuo and dissolved in methanol (50 ml). At −78° C., this was mixed with sodium borohydride (620 mg) and warmed up to 0° C. and stirred for one hour. This solution is was poured into water (50 ml) and extracted with ethyl acetate (2×100 ml). The organic extracts were washed with brine, dried over sodium sulfate, filtered and concentrated. The crude material was purified on a silica gel column (hexane:ethyl acetate, 1:1) to provide alcohol 46 (1.95 g, 38% yield). Much high yield (>90%) of the alcohol 46 is obtained if sodium triacetoxyborohydride is used instead of sodium borohydride.

A solution of above alcohol 46 in pyridine (10 ml) and p-toluenesulfonylchloride (1.75 g) was stirred at 0° C. for 14 hours. This mixture was quenched with water (20 ml) and Stirred for 20 minutes. This mixture was acidified with 6N of hydrochloride solution and extracted with ethyl acetate (2×100 ml). The combined organic extracts were then washed water (100 ml), saturated sodium bicarbonate (30 ml), brine (30 ml), dried over sodium sulfate, filtered and concentrated to provide the crude tosylate 47. This crude tosylate was heated with sodium iodide (3 g) in acetone (40 ml) at 45° C. for 2 hours. After cooling, the mixture was evaporated and the residue worked up with water (50 ml) and ethyl acetate (200 ml). The crude was purified on a silica gel column (hexane:ethyl acetate, 2:1) to provide the iodide 48 (2.9 g, 76%).

EXAMPLE 18

Preparation of 1-Deoxy-1-α-(2-Carboxy-Naphthyl-6-Oxyethyl)-L-Fucose (51)

A solution of ethyl 6-hydroxyl-2-naphthate (49, 89 mg, 0.42 mmole) and iodide (48, 177 mg, 0.42 mmole)in dimethylforamide (1 ml) was stirred with potassium carbonate (174 mg) for 14 hours. The reaction mixture was worked up with water (30 ml) and ethyl acetate (100 ml). The organic layer was washed with brine (30 ml), dried over sodium sulfate, filtered and concentrated. The crude was purified on a silica gel column (hexane:ethyl acetate, 4:1) to provide naphthate 50 (120 mg, 55%).

A solution of naphthate 9 in methanol (30 ml) stirred with 1N sodium hydroxide (3 ml) for 4 hours. The mixture was acidified with 6N hydrochloride and solid collected by filtration. This solid was washed with water, ethyl acetate and suction dried to provide naphthoic acid 51 (24 mg).

EXAMPLE 19

Preparation of 2-Carboxy-5-Hydroxy-7-(1-Deoxy-1-α-Fucosyl-Ethyleneoxy)-4-Methoxy Isoflavone (54)

A solution of 2-carboethoxy-5,7-dihydroxy-4'-methoxy-isoflavone (52, 166 mg, 0.47 mmole) and the iodide 48 (200 mg, 0.47 mmole) in dimethylforamide (1 ml) was stirred with potassium carbonate (265 mg) for 14 hours. The mixture was worked up with water (50 ml) and ethyl acetate (2×100 ml). The combined organic extracts were washed with brine, dried over sodium sulfate, filtered and concentrated. The crude was purified on a silica gel column (hexane:ethyl acetate, 1:1) to provide the isoflavone 53 (265 mg, 86%).

A solution of isoflavone 53 (250 mg) in methanol (3 ml) and tetrahydrofuran (1 ml) was stirred in 1N sodium hydroxide (3 ml) for 2 hours. All the volatiles were removed and the resulting aqueous solution acidified with 1N hydrochloride. Solid was collected, washed with water and ethyl acetate and dried by suction filtration to provide the isoflavone 54 (135 mg, 71%).

EXAMPLE 20

Preparation of 3,7-Di-(1-Deoxy-1-α-Fucosyl-Ethyleneoxy)-2-Naphthoic Acid (57)

A solution of ethyl 3,7-dihydroxy)-2-naphthoate (55, 62 mg, 0.26 mmole) and iodide 48 (242 mg) in dimethylforamide (0.5 ml) was heated at 55° C. with potassium carbonate (175 mg) for 4 hours. An additional amount of the iodide 48 (80 mg) was added to the mixture which was heated at 55° C. overnight. The mixture was worked up with water (50 ml) and ethyl acetate (2×75 ml). The ethyl acetate extracts were washed with brine (30 ml), dried over sodium sulfate, filtered and concentrated. The crude material was purified on a silica gel column (hexane:ethyl acetate, 1.5:1) to provide the naphthoate 56 (130 mg, 63% yield).

A solution of naphthoate 56 (120 mg) in methanol (1 ml) was stirred with of 2N potassium hydroxide (1.1 ml) at room temperature overnight. This mixture was acidified with 6N hydrochloride solution and concentrated to dryness. The residue was dissolved in methanol (10 ml) and solid removed by filtration. The filtrate was concentrated to provide naphthoic acid 57 (70 mg).

EXAMPLE 21

Preparation of 3,5-Di-(1-Deoxy-1-α-Fucosyl-Ethyleneoxy)-2-Naphthoic Acid (58)

When ethyl 3,5-dihydroxy-2-naphthoate is substituted for ethyl 3,7-dihydroxy-2-naphthoate in Example 20, the identical process afforded the naphthoic acid 58.

EXAMPLE 22

Preparation of 6-(1-Deoxy-1-α-Fucosyl-Ethyleneoxy)-α-Methyl-2-Naphthalene Acetic Acid (61)

The iodide 48 (286.6 mg) and 6-hydroxy-α-methylnaphthoacetic acid methyl ester 59 (154.0 mg) were dissolved in dimethylforamide (3 ml) and potassium carbonate (277.6 mg) was added. The reaction was stirred at room temperature for 12 hours, after which it was partitioned between water (10 ml) and ethyl acetate (50 ml). The layers were separated and the organics were washed with water (3×10 ml) and brine (10 ml). The organic layer was dried over magnesium sulfate, filtered and concentrated to dryness. Purification of the residue on silica gel (25% ethyl acetate/hexane) gave the desired product 60 (225.8 mg, 64% yield).

The above product 60 was dissolved in methanol (1.70 ml) and 2N sodium hydroxide solution (1.70 ml) was added. The reaction was stirred at room temperature for 13 hours, after which it was acidified with 6N hydrochloride. After concentrating to dryness, the residue was washed with water and dried under vacuum to give the desired product 61 (167 mg, 100% yield).

EXAMPLE 23

Preparation of 6-Glyceroxy-α-Methyl-2-Naphthalene Acetic Acid (65)

Glycidol 62 (2.95 ml) and 6-hydroxy-α-methylnaphthoacetic acid methyl ester 59 (1.02 g) were dissolved in dimethylforamide (10 ml). Potassium carbonate (3 g) was added and the reaction was stirred at room temperature for 3 days. After diluting with ethyl acetate (100 ml), the reaction was washed with water (5×10 ml). The water layer was washed with ethyl acetate (20 ml) and the combined ethyl acetate layers were washed with brine (20 ml). After concentrating, the residue was purified on silica gel (70% ethyl acetate/hexane) to give the desired methyl ester glycidol adduct 63 (251.5 mg, 19% yield) and the glycidyl ester glycidol adduct 64 (200.3 mg, 13% yield).

The glycidyl ester glycidol adduct 64 was dissolved in methanol (0.6 ml) and 2N sodium hydroxide (0.6 ml) was added. The reaction was stirred at room temperature for 23 hours and acidified with 6N hydrochloride. After concentrating the mixture to dryness, the residue was washed with water and dried under vacuum to give the desired product 65 (125.9 mg, 75% yield).

EXAMPLE 24

Preparation of 1-Deoxy-1-α-(p-Carboxy-Phenoxyethyl)-L-Fucose (67)

p-Hydroxybenzoic acid ethyl ester (0.1 g, 0.63 mmol) and potassium carbonate (0.2 g, 1.6 mmol) were added to a solution of compound 48 (0.22 g, 0.5 mmol) in DMF (1 ml), and the mixture was stirred at room temperature for 22 h. Water (1 ml) was added and the mixture was washed with 30% ethyl acetate/hexane (3×5 ml), the combined organic phases were dried (MgSO$_4$), filtered, and concentrated. The residue was purified on silica gel (20% ethyl acetate/hexane then 40% ethyl acetate/hexane) to give the coupled product (66, 0.23 g, 93% yield).

Compound 66 (0.2 g, 0.45 mmol) was dissolved in MeOH (1.8 ml) and 2N aq. NaOH (1.8 ml) was added. After stirring at room temperature (32 h), the reaction mixture was acidified with 6N aq. HCl (2 ml) and concentrated to dryness. The residue was suspended in water (2 ml) and refrigerated for 16 h, filtered and washed with water (2×2 ml). The solids were collected and dried under vacuum to give the title compound 67 (87.8 mg, 62% yield).

EXAMPLE 25

Preparation of 1-Deoxy-1-α-(o-Carboxy-Phenoxyethyl)-L-Fucose (68)

When o-hydroxybenzoic acid ethyl ester is substituted for p-hydroxybenzoic acid ethyl ester in Example 24, the identical process afforded the naphthoic acid 68.

EXAMPLE 26

Preparation of 1-Deoxy-1-α-(m-Carboxy-Phenoxyethyl)-L-Fucose (69)

When m-hydroxybenzoic acid ethyl ester is substituted for p-hydroxybenzoic acid ethyl ester in Example 24, the identical process afforded the naphthoic acid 69.

EXAMPLE 27

1-Deoxy-α-1-Acetylenyl-2,3,4-tri-O-Benzyl-I-Fucose (71)

A solution of 1-O-acetyl-2,3,4-tri-O-benzyl-L-fucose (10 g, 21 mmol) and bistrimethylsilylacetylene (7.16 g, 42 mmol) in dichloromethane (50 ml) was cooled to −20° C. under argon. A solution of tin tetrachloride in dichloromethane (21 mmol, 1M) was added and the mixture was stirred at −20° C. for 1 hour. The reaction was quenched with saturated aqueous sodium bicarbonate (50 ml), extracted with ethyl acetate (3×50 ml) and the combined organic layers were washed with saturated aqueous sodium bicarbonate (2×10 ml) and brine (20 ml), dried (MgSO$_4$), filtered and concentrated, the residue was purified on silica gel (30% ethyl acetate/hexane) to give the silylacetylenyl fucose (70, 8.1 g, 75% yield).

Water (10 ml) followed by potassium flouride (9.16 g, 1.58 mmol) was added to a solution of compound 70 (8.1 g, 15.76 mmol) in DMF (30 ml). The mixture was stirred at room temperature (2 h), diluted with water (100 ml) and extracted with 30% ethyl acetate/hexane (3×50 ml). The combined organic layers were washed with brine (50 ml), dried (MgSO$_4$), filtered and concentrated to give compound 71 (6.97 g, 100% yield).

EXAMPLE 28

Preparation of 1-Deoxy-1-α-(m-Carboxy-Phenylethyl)-L-Fucose-Phenylalanine Amide (74)

Carbonyl diimidazole (2.62 g, 16.14 mmol) was added to a solution of m-iodobenzoic acid (4 g, 16.14 mmol) in tetrahydrofuran (100 ml), and the mixture was stirred at room temperature (45 min). Phenylalanine benzyl ester p-toluenesulfonate (6.90 g, 16.14 mmol) was added, the mixture was stirred (18), and concentrated to dryness. The residue was extracted with ethyl acetate (50 ml). The organic phase was washed with 1N aq. HCL (3×20 ml), saturated aqueous sodium bicarbonate (2×20 ml) and brine (20 ml), dried (MgSO$_4$) and concentrated to give the amide 72 (4.79 g, 61% yield).

The amide 72 (1.28 g, 2.63 mmol) and compound 71 (1.16 g, 2.63 mmol) were dissolved in DMF (10 ml). Triethylamine (0.73 ml, 5.26 mmol) was added followed by tetrakistriphenyl-phosphine palladium (100 mg) and copper (I) iodide (40 mg). The reaction was stirred at room temperature (6 h), diluted with water (100 ml), and extracted with ethyl acetate (3×20 ml). The combined organic phases were washed with 1N aq. HCl (40 ml), saturated aqueous sodium bicarbonate (40 ml) and brine (40 ml), dried (MgSO$_4$) and concentrated. The residue was purified on silica gel (20% ethyl acetate/hexane) to give the coupled product 73 (0.6 g, 28% yield).

Compound 73 (0.6 g, 0.75 mmo) was dissolved in ethyl acetate (5 ml). 10% Palladium/carbon (0.6 g) was suspended in methanol (40 m) and the ethyl acetate solution was added via cannula. After stirring under hydrogen for 4 days, the mixture was filtered through Celite and the filtrate was concentrated to dryness giving the title compound 74 (0.24 g, 72% yield).

EXAMPLE 29

Preparation of 1-Deoxy-1-α-(p-Carboxy-Phenylethyl)-L-Fucose-Phenylalanine Amide (75)

When p-iodobenzoic acid is substituted for m-iodobenzoic acid in Example 27, the identical process afforded the amide 75.

EXAMPLE 30

Preparation of 1-Deoxy-1-α-(o-Carboxy-Phenylethyl)-L-Fucose-Phenylalanine Amide (76)

When o-iodobenzoic acid is substituted for m-iodobenzoic acid in Example 27, the identical process afforded the amide 76.

EXAMPLE 31

Preparation of Synthesis of 6-O-sulfo-hexanyl-α-L-fucopyranoside (77)

Pyridine-SO$_3$ (1.3 g, excess) was added into a solution of 6-hydroxyhexyl-2,3,4-tri-O-benzyl-α-L-fucopyranoside (2.5 g) in N,N-DMF (15 ml) and the solution was stirred under a nitrogen atmosphere at 50° C. for 4 h until the TLC (20:1 toluene-acetone) indicated the absence of any starting material. The solution was neutralized with IR 120 (Na+), filtered and purified on a silica gel column (10:1:1 toluene-acetone-methanol). The syrupy product obtained by evaporation of the appropriate fractions was hydrogenated with 10% Pd-C in 10% aq. methanol. The reaction mixture was filtered, evaporated and the product was eluted from a biogel P2 column. Appropriate fractions were pooled and lyophilized to give the title compound 77 (600 mg), molecular formula $C_{12}H_{23}O_9NaS$ (366.4). Found: 365.2 (M–H)–, 343.2 (M–Na)–.

EXAMPLE 32

Selectin Binding

An ELISA assay was employed that uses recombinant fusion proteins composed of extracellular portions of the human selectins joined to human immunoglobulin heavy chain CH$_3$, CH$_2$, and hinge regions. See, for example, Walz et al., *Science* (1990) 250:1132; Aruffo et al., *Cell* (1991) 67:35; Aruffo et al., *Proc. Natl. Acad. Sci. USA* (1992) 89:2292. The assay is well known in the art, and generally consists of the following three steps:

I. 2,3 sLe$^x$ glycolipid (25 picomole/well) was transferred into microtiter wells as solutions and then evaporated off. Excess, which remained unattached, was washed off with water. The wells were then blocked with 5% BSA at room temperature for an hour and then washed with PBS containing 1 mM calcium.

II. Preparation of "multivalent" receptor of the Selectin-IgG chimera was carried out by combining the respective chimera 1 μg/ml) with biotin labelled goat F(ab')$_2$ anti-human IgG (Fc specific) and streptavidin-alkaline phosphatase diluted 1:1000 in 1% BSA-PBS (1 mM calcium) and incubating at 37° C. for 15 min. This allowed the soluble multivalent receptor complex to form.

III. Potential inhibitors such as compounds of formula I or II were allowed to react with the soluble receptor at 37° C. for 45 min. This test assumes that optimal binding, between the soluble phase receptor complex and the inhibitor (non natural ligand), would have occurred within this time frame. This solution was then placed in the microtiter wells that were prepared in step I. The plate was incubated at 37° C. for 45 minutes to allow the soluble receptor to bind to its natural ligand. In the presence of a strong inhibitor only a few receptors should be free to bind to the microtiter plate coated with the natural ligand.

The positive control is the signal produced by the soluble receptor when it is allowed to react with 2,3 sLe$^x$ glycolipid in the microtiter wells in the absence of any inhibitor. This was considered 100% binding. The signal produced by the receptor that had been previously treated with an inhibitor (recorded as O.D.), was divided by the signal produced by the positive control and multiplied by 100 to calculate the % receptor bound to the well, or as expressed in the figures, the per cent of control binding. Several of the compounds described herein were tested using this assay. Table 1 lists the extent to which the invention compounds inhibit binding of E, L and P-selectin to 2,3 sLex glycolipid in terms of IC$_{50}$ values.

TABLE 1

Selectin activity of Compounds of structural formula I and II

| Compound | E-selectin (mM) | L-selectin (mM) | P-selectin (mM) |
|---|---|---|---|
| 7 | >4 | 1–3 | >4 |
| 10 | 2–3 | 2–3 | ~0.5 |
| 28 | >4 | — | — |
| 32 | 2 | ≦4 | — |
| 51 | <0.5 | <1 | <0.5 |
| 54 | <0.5 | >4 | <0.5 |
| 57 | >4 | ~2 | <0.5 |
| 58 | >4 | ~4 | 2 |
| 60 | >4 | 4 | >2 |
| 64 | >4 | >4 | >4 |
| 67 | <0.5 | >2 | <0.5 |
| 68 | ~4 | >4 | <0.5 |
| 69 | >4 | >4 | >4 |
| 74 | >4 | >4 | >4 |
| 75 | >4 | >4 | 4 |
| 76 | >4 | >4 | >4 |
| 77 | 2–3 | 2–3 | ~0.5 |

Figure 5:
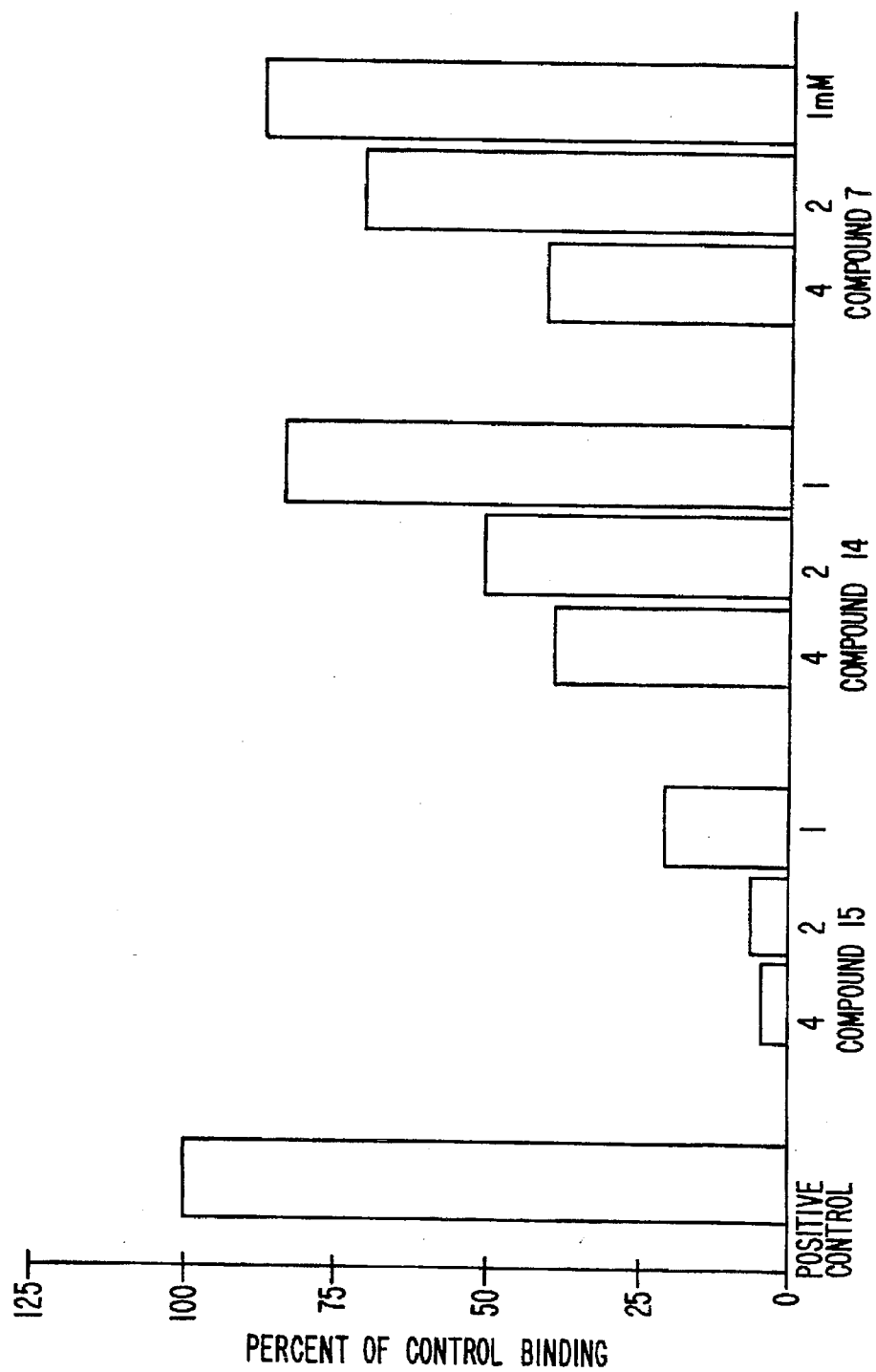
FIG. 5 is a graph showing the results of Elisa assays carried out to determine the ability of three different compounds to block the binding of 2,3,sialyl-Le$^x$ to L-selectin IgG chimera. The compounds tested were 7, 14 and 15. The compounds were tested at several concentrations as shown in the figure. The results are expressed as per cent of control binding.

The results shown in FIG. 4 indicate that 7 and 14 inhibit E-selectin binding to 2,3 sLe$^x$ glycolipid. FIG. 5 shows that 7 and 14 also inhibit L-selectin binding in a concentration dependent manner. Further, the figure also shows that 15 blocks L-selectin binding at concentrations lower than 7 and 14.

The structures of 7, 14, and 15, are shown below:

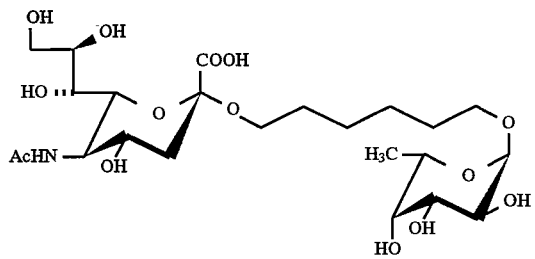

-continued

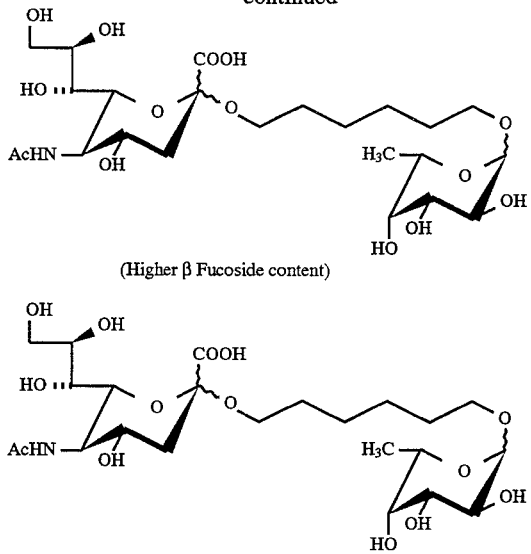

(Higher β Fucoside content)

Figure 6:
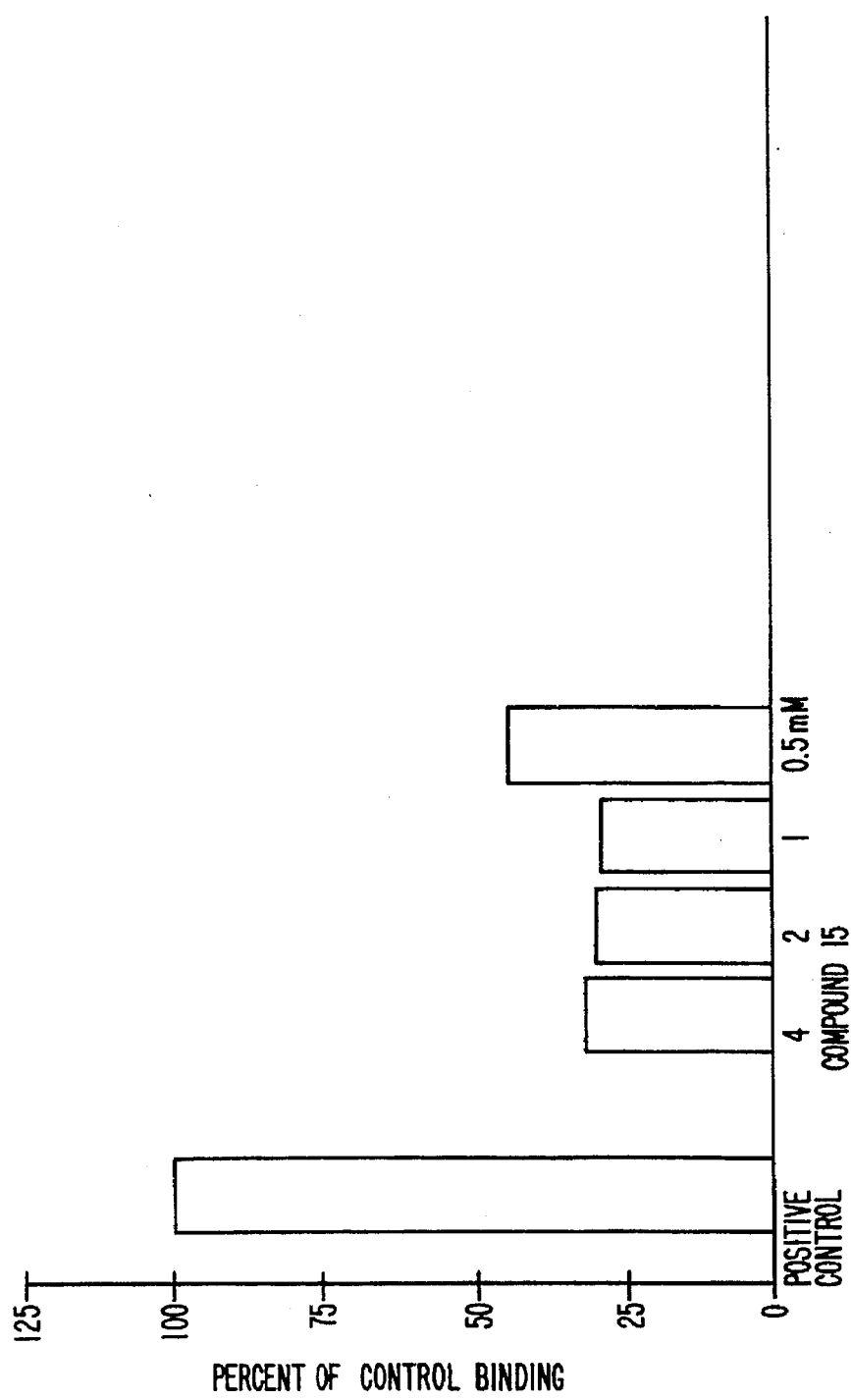
FIG. 6 is a graph showing the results of Elisa assays carried out to determine the ability of compound 10 to block the binding of 2,3,sialyl-Le$^x$ to L-selectin IgG chimera. The results are expressed as per cent of control binding.

The results shown in FIG. 6 indicate that the compound 10 inhibits L-selectin binding to 2.3 sLe$^x$ glycolipid. Note that at all four concentrations of the compound tested there is significant inhibitory activity. The structure of 10 is shown below:

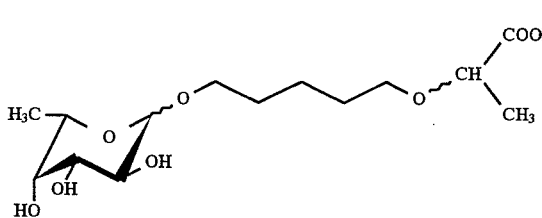

In addition to the ligands described above, other ligands could be obtained by selecting more rigid spacers in order to maintain the appropriate statistical average distance between the sialic acid and fucose moieties in space thereby improving the inhibitory property of such structures towards the selectins. Further modifications of these compounds e.g., attaching them through chemical linkages on appropriate molecular supports and use of analogs or derivatives of sialic acid and L-fucose are also considered to be within the scope of the present invention.

EXAMPLE 33

Flow Cytometric Assay for P-selectin Ligand

The interaction of P-selectin and its cellular ligand was studied using a flow cytometric assay (Erbe, D. V. et al., *J. Cell Biol.* (1993) 120:1227). HL60 cells (maintained in high glucose DME plus 10% Hyclone FBS) were used in this assay. Before staining with P-selectin-IgG the cells were preincubated in Dulbecco's PBS/1% BSA/0.1% sodium azide/1% normal rabbit serum (staining medium) for 30–60 mins on ice. After this initial incubation, 1 µg of P-selectin-IgG was added to 100 µl aliquots of 10$^6$ cells and incubated for 30–60 mins on ice. The cells were when washed with staining medium and resuspended in 100 µl of staining medium to which was added 2 µl of a phycoerythrin-conjugated F(ab')$^2$ goat anti-human IgG (Fc specific). The cells were incubated for 15–30 mins on ice, washed twice with staining medium, and resuspended in 0.5 ml of staining medium before flow cytometric analysis on a FACScan (Becton Dickinson & Co., Mountain View, Calif.). To determine that the staining was an interaction of P-selectin with its ligand, the staining was also done in the presence of 10 mM EGTA. To determine the protease sensitivity and the requirement for sialic acid of this interaction, HL-60 cells in D-PBS and 1% BSA were incubated with either trypsin or Arthrobacter or Clostridium sialidases at 37° C. before resuspending in staining medium. To examine the ability of various carbohydrates to inhibit staining, 50 µg/ml fucoidin (Sigma Immunochemicals, St. Louis, Mo.), 50 µg/ml dextran sulfate (Pharmacia Fine Chemicals, Piscataway, N.J.), 10 mg/ml mannose-1-phosphate (Sigma Immunochemicals), or 10 mg/ml mannose-6-phosphate (Sigma Immunochemicals) was added to cells immediately before the addition of the P-selectin chimera. Each carbohydrate was then present until the cells were washed before the addition of the second stage antibody. A potential complication of this FACS assay arose from the use of selectin-IgG chimeras to stain cells which bear human IgG Fc receptors (FcγR; Fanger, M. W., et al., *Immunol. Today* (1989) 10:92). Adding rabbit IgG (in the form of normal rabbit serum) to the assay medium blocked this binding in most cases. Table 2 shows the results (in terms of % inhibition) of the ability of compounds 7 and 77 to inhibit P-selectin-IgG binding to HL-60 cell lines.

TABLE 2

| Compound # | Concentration (mg/ml) | Inhibition (%) |
|---|---|---|
| 7 | 10 | 60 |
|   | 50 | 80 |
|   | 100 | 80 |
| 77 | 10 | 50 |
|   | 100 | 50 |
|   | 200 | 60 |

EXAMPLE 34

Treatment of Sepsis

A number of the complications associated with sepsis arise from unwanted neutrophil extravasation and adhesion of the neutrophils to the endothelium. The invention compounds 10, 14 and 15 would be used to prevent or treat sepsis.

The effectiveness of these compounds would be shown in a baboon sepsis model system as described by Taylor et al., *J. of Clinical Inv.*, (1987), 79:918, and by Taylor, et al., *Circulatory Shock*, (1988), 26:227. Briefly, this would consists of determining if the compounds are effective in treating sepsis by preventing the death, or prolonging the lives of septic animals to either a lethal or sublethal dose of *E. coli*. A lethal or sublethal dose of *E. Coli* consist of approximately 4×10$^{10}$ and 0.4—10$^{10}$ organisms, respectively. Baboons that receive a lethal dose of *E. Coli* invariably die within 16–32 hours. Taylor, et al., *J. of Clinical Inv.*, (1987), 79:918, and Taylor, et al., *Circulatory Shock*, (1988), 26:227.

Thus, the procedure would consist of using two administration routines for each of the three compounds wherein they are delivered in physiological saline. In the first, between 1 and 10 mg of compound per kg of body weight is administered in three separate doses at 24, 22, and 21 hours before a lethal challenge of bacteria. Alternatively, compound can be administered in a single dose simultaneously with the bacterial challenge. In both instances the compounds would considerably extend the lifetime of the baboons that receive the multiple or single dose treatment and they would survive well beyond 48 hours.

EXAMPLE 35

Treatment of Peritonitis

Certain of the invention compounds have been shown to be efficacious in treating peritonitis. The efficaciousness of 7 and 10 was shown using a murine thioglycollate induced peritonitis model. The assay materials and methods are known in the art, or are generally described by Lewinsohn, D. et al., *J. Immun.*, 138:4313–4321 (1987), or Watson, S. et al., *Nature* 349:164–166 (1991).

This assay measures the ability of the compounds to inhibit neutrophil migration to the peritoneal cavity, the migration being initiated by the presence of thioglycollate in the peritoneal cavity. Thioglycollate is a known and effective inflammatory agent that causes neutrophil migration into the mouse peritoneum when it is administered intraperitoneally. Lewinsohn, D. et al., *J. Immun.* (1987) 138:4313–4321.

Briefly, female Swiss Webster mice weighing about 25 grams were injected in the tail vein with 200 µl of phosphate buffered saline (PBS) with or without the appropriate compound. The pH of the solutions was adjusted to neutrality by the addition of either NaOH or HCL and sterilized by filtration through a 0.2 µ filter.

Immediately following injection with the appropriate compound or PBS, the mice were injected intraperitoneally with 1 ml of thioglycollate medium prepared as described by the manufacturer, BBL. Three hours following injection of the thioglycollate solution the mice were sacrificed by $CO_2$ asphyxiation, and the number of cells in the peritoneum removed by lavage with 5 ml of heparinized (5 U/ml) 0.9% sodium chloride solution containing 0.1% bovine serum albumin. Cell number was determined using a Coulter Counter. The cells were prepared for counting by diluting the lavage fluid with 1:50 of a commercial physiological isotonic solution, Isoton II, and the cells lysed by adding S/P Lysing and Hemoglobin Reagent (1:100 final dilution). Cell nuclei were counted in a sized window with lower and upper limits set at 3.9 and 5.7 µm, respectively.

Figure 7B:
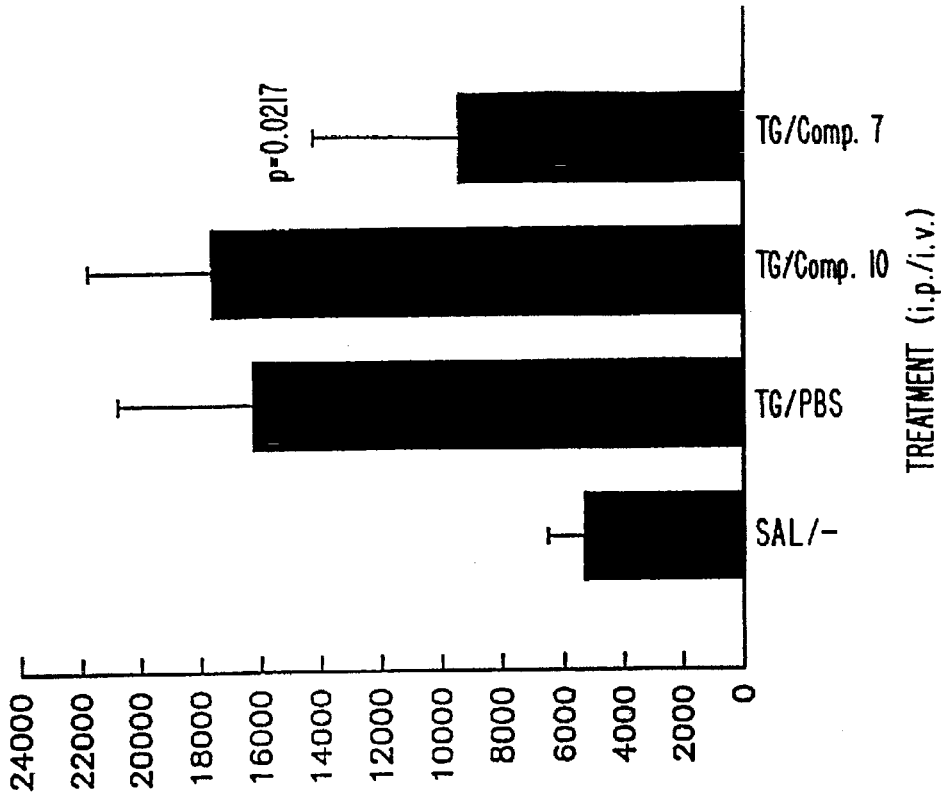
FIG. 7(b) shows the effect of compounds GM 1221 and GM 1398 on thioglycollate induced peritonitis.
Figure 7A:
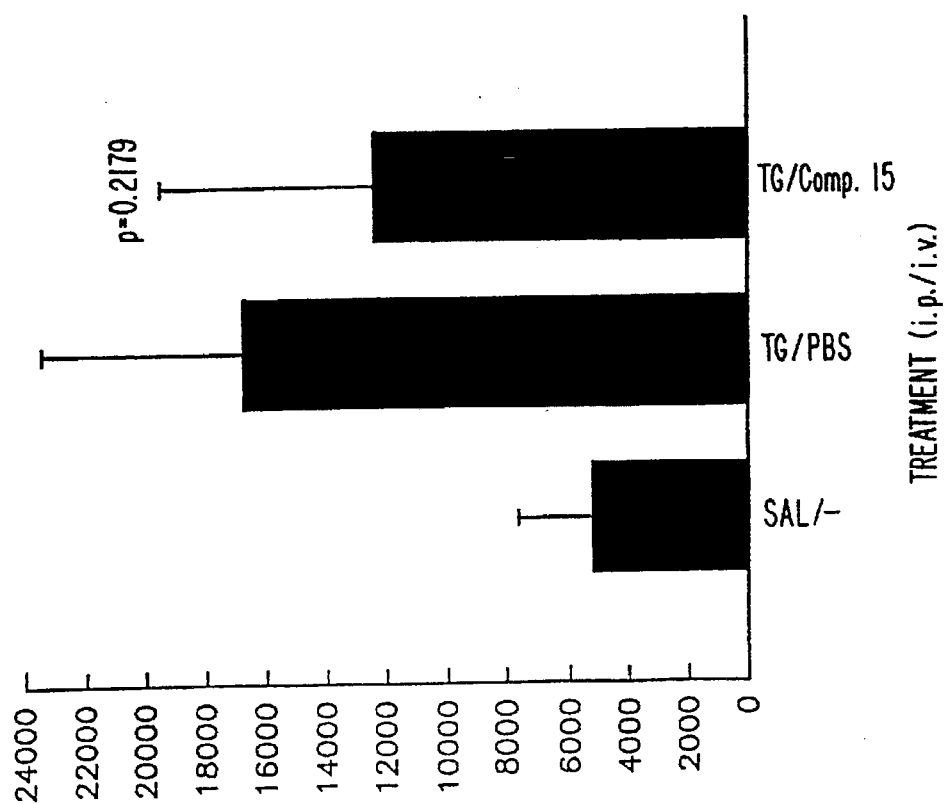
FIG. 7(a) shows the effect of compound GM1221 on thioglycollate induced peritonitis. Mice were injected with (1) saline alone (sal/-), (2) thioglycollate plus phosphate buffered saline (TG/PBS), or (3) thioglycollate and GM 1221 (TG/GM 1221) and the number of neutrophils in the peritoneal cavity were measured.

FIG. 7(a) and (b) show the results. It is apparent that both 7 and 10 inhibit neutrophil migration into the peritoneum. However, the better compound is 7 which inhibited about 30% more neutrophil migration than 10.

EXAMPLE 36

Reperfusion Injury Assay

Experiments were done to determine the effectiveness of compound 7 in decreasing adhesion of human neutrophils in the rabbit isolated heart. Addition of the human plasma to the rabbit isolated heart results in activation of the complement components found within the plasma, which in turn promotes an increase in the neutrophil accumulation. This model is used to determine the effect of $sLe^x$ analogues on inhibiting complement-induced neutrophil adhesion.

Hearts from New Zealand White rabbits were excised, mounted on a modified Langendorff apparatus and perfused with Krebs-Heinseleit buffer. Cardiac functional parameters were monitored upon a Grass Model 79D polygraph machine. 4% normal human plasma (NHP) was added to the recirculating buffer. Ten minutes after the addition of the plasma, 13b (0.1 mg/ml) was added to the perfusate. After 15 minutes of perfusion with the plasma, 51-chromium labelled human neutrophils ($1 \times 10^5$/ml) were added to the perfusate and allowed to recirculate for an additional 15 minutes. At the end of this time the hearts were washed with fresh buffer to remove non-specifically bound neutrophils, dried and counted in a well type gamma-counter. A concentration response curve was generated using concentrations of 0.001, 0.01 and 0.1 mg/ml. Six hearts were used for each of these concentrations.

Table 3 lists the results, expressed as the percent inhibition of neutrophil accumulation. These results are expressed as the number of radiolabelled human neutrophils/mg of dry weight of the heart.

It should also be noted that the greatest degree of inhibition seen using pharmacological agents, including a number of peptides derived form P-selectin and antibodies directed against P-selectin and the CD11 b/CD18 complex (Ma, Xin-liang, et al., *Circulation* (1993) 88–2:649), has been 40%. Compound 7 provides a degree of inhibition (30%) similar to any of the pharmacological agents tested thus far.

Based on the above results, it is apparent that the compounds of the invention are useful for treating diseases, preferably diseases that have an inflammatory component, Adult Respiratory Distress Syndrome (ARDS), ischemia and reperfusion injury, including strokes, mesenteric and peripheral vascular disease, organ transplantation, and circulatory shock (in this case one or many organs might be damaged following restoration of blood flow).

TABLE 3

| Compound | % Neutrophil Inhibition |
|---|---|
| 7 | 30 |

The instant invention is shown and described herein in what is considered to be the most practical and preferred embodiments. Publications listed herein are incorporated herein by reference to disclose specific procedures on how to make, and/or use the invention. Further, it is recognized that departures may be made therefrom which are within the scope of the invention, and that obvious modifications will occur to one skilled in the art upon reading this disclosure.

What is claimed:

1. A compound comprising the following structural formula II:

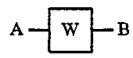

where W is selected from a group consisting of structures a–d below:

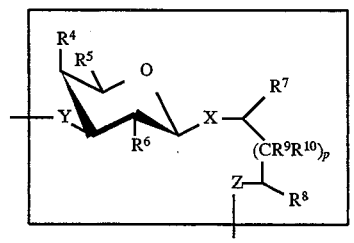

(a)

-continued

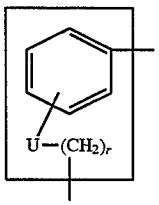
(b)

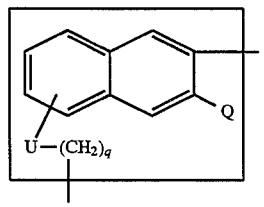
(c)

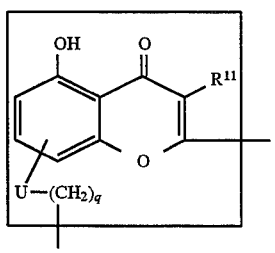
(d)

wherein p is an integer of from 0–2, q is an integer of from 0–3, and r is an integer of from 0–5;

A is selected from the group consisting of α and β forms of sialic acid, Kemp's acid, quinic acid, R and S forms of mandelic acid, R and S forms of glyceric acid, R and S forms of lactic acid, propionic, formic and acetic acid, and esters and amides thereof, —$SO_3$, sulfonate, —$PO_3$, phosphonate, trifluoromethyl, diazine and triazine;

B is selected from a group consisting of α and β forms of fucose, arabinose and esters and substituted forms thereof wherein one or more of the OH groups is independently replaced by F, $N_3$, NHAc, $NHCOCF_3$, wherein B is covalently bound to W at a substituent selected from the group consisting of Z, U—$(CH_2)r$ and U—$(CH_2)q$;

X, Y, Z=$CH_2$, N, O, S, SO, or $SO_2$;
U=O or —$CH_2$;
Q=H or —X—$(CH_2)_q$B;
$R^4$=H, OH, or F;
$R^5$=H, or $CH_2$—$R^4$;
$R^6$=H, OH, NHAc, or $NHCOCF_3$;
$R^7$ and $R^8$ may independently =H, —$COR^{12}$, —$CH_2$—O—$(CH_2)_s$—$SO_2$—$(CH_2)_s$—NHG, —$CH_2$—O—$(CH_2)_s$—NH—$(CH_2)_s$—CH(NHG)—$COOR_1$, —$CH_2$—O—$(CH_2)_s$—CHO, —$CH_2$—O—$(CH_2)_s$—$(CHR^{13})_s$—$(CH_2R^{13})$, wherein s is an integer of from 1–10, or $R^7$ and $R^8$ taken together form a five or six membered ring;
$R^9$, $R^{10}$ are independently H or OH, or $R^9$ and $R^{10}$ taken together form an oxo group;
$R^{11}$=H, 1–6C alkyl, halogen, OH, O-alkyl, or O-aryl;
$R^{12}$=OH, 2–10C alkoxy chain, 2–10C alkylamine, peptide, or OM where M is a counterion;
$R^{13}$=OCO—$(CH_2)_t$—$CH_3$, wherein t is an integer of from 3–18; and G=a peptide, —$COR^{14}$ or —$SO_2R^{14}$, wherein $R^{14}$=an aryl, alkyl, alkenyl or alkynyl group.

2. A compound of claim 1 wherein A is selected from the group consisting of sialic acid, Kemp's acid, quinic acid, glyceric acid, lactic acid, propionic, formic and acetic acid, and esters and amides thereof, sulfate, sulfonate, phosphate, phosphonate, trifluoromethyl, diazine and triazine, and B is selected from the group consisting of fucose, arabinose and esters and substituted forms thereof, wherein the substituted forms have at least one OH that is replaced by F, $N_3$, NHAc or $NHCOCF_3$.

3. A compound of claim 2 wherein A is sialic acid, B is fucose and W is

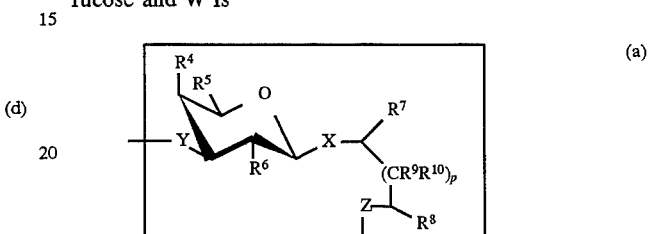
(a)

4. A composition, comprising a mixture of at least two compounds of claim 1.

5. A pharmaceutical composition, comprising a pharmaceutically acceptable carrier and a therapeutically effective amount of a compound having the following formula II:

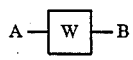

where W is selected from a group consisting of structures a–d below:

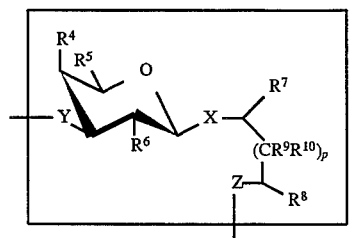
(a)

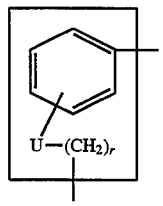
(b)

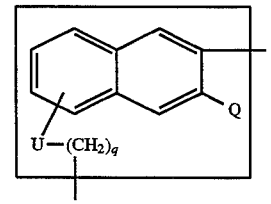
(c)

(d)

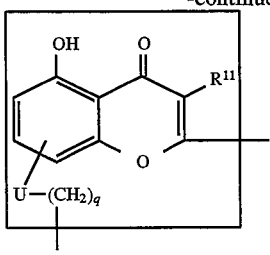

wherein p is an integer of from 0–2, q is an integer of from 0–3, and r is an integer of from 0–5;

A is selected from the group consisting of α and β forms of sialic acid, Kemp's acid, quinic acid, R and S forms of mandelic acid, R and S forms of glyceric acid, R and S forms of lactic acid, propionic, formic and acetic acid, and esters and amides thereof, —SO$_3$, sulfonate, —PO$_3$, phosphonate, trifluoromethyl, diazine and triazine;

B is selected from a group consisting of α and β forms of fucose, arabinose and esters and substituted forms thereof wherein one or more of the OH groups is independently replaced by F, N$_3$, NHAc, NHCOCF$_3$, wherein B is covalently bound to W at a substituent selected from the group consisting of Z, U—(CH$_2$)$_r$ and U—(CH$_2$)$_q$;

X, Y, Z=CH$_2$, N, O, S, SO, or SO$_2$;

U=O or —CH$_2$;

Q=H or —X—(CH$_2$)$_q$B;

R$^4$=H, OH, or F;

R$^5$=H, or CH$_2$—R$^4$;

R$^6$=H, OH, NHAc, or NHCOCF$_3$;

R$^7$ and R$^8$ may independently=H, —COR$^{12}$, —CH$_2$—O—(CH$_2$)$_s$—SO$_2$—(CH$_2$)$_s$—NHG, —CH$_2$—O—(CH$_2$)$_s$—NH—(CH$_2$)$_s$—CH(NHG)—COOR$_1$, —CH$_2$—O—(CH$_2$)$_s$—CHO, —CH$_2$—O—(CH$_2$)$_s$—(CHR$^{13}$)$_s$—(CH$_2$R$^{13}$), wherein s is an integer of from 1–10, or R$^7$ and R$^8$ taken together form a five or six membered ring;

R$^9$, R$^{10}$ are independently H or OH, or R$^9$ and R$^{10}$ taken together form an oxo group;

R$^{11}$=H, 1–6C alkyl, halogen, OH, O-alkyl, or O-aryl;

R$^{12}$=OH, 2–10C alkoxy chain, 2–10C alkylamine, peptide, or OM where M is a counterion;

R$^{13}$=OCO—(CH$_2$)$_t$—CH$_3$, wherein t is an integer of from 3–18; and

G=a peptide, —COR$^{14}$ or —SO$_2$R$^{14}$, wherein R$^{14}$=an aryl, alkyl, alkenyl or alkynyl group.

6. A pharmaceutical composition of claim 5, wherein the compound binds to E-selectin.

7. A pharmaceutical composition of claim 5, wherein A is sialic acid, B is fucose or an ester thereof and W is (a)

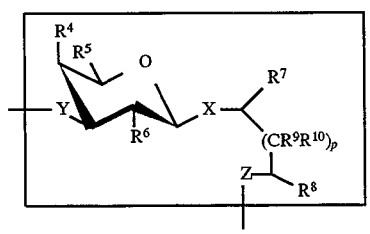

8. A pharmaceutical composition of claim 5, wherein the composition includes a mixture of more than one compound of formula II.

9. A method of treating a selection-mediated disorder in a subject in need thereof, comprising administering to the subject a therapeutically effective amount of a pharmaceutical composition comprising a pharmaceutically acceptable carrier and a compound having the following structural formula II:

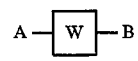

where W is selected from a group consisting of structures a–d below:

(a)

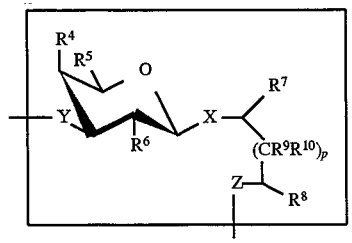

(b)

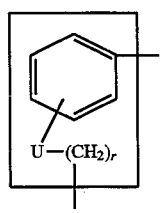

(c)

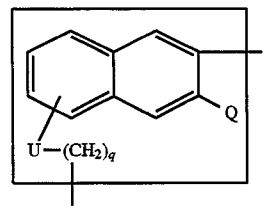

(d)

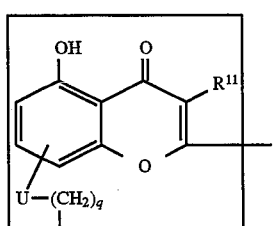

wherein p is an integer of from 0–2, q is an integer of from 0–3, and r is an integer of from 0–5;

A is selected from the group consisting of α and β forms of sialic acid, Kemp's acid, quinic acid, R and S forms of mandelic acid, R and S forms of glyceric acid, R and S forms of lactic acid, propionic, formic and acetic acid, and esters and amides thereof, —SO$_3$, sulfonate, —PO$_3$, phosphonate, trifluoromethyl, diazine and triazine;

B is selected from a group consisting of α and β forms of fucose, arabinose and esters and substituted forms thereof wherein one or more of the OH groups is independently replaced by F, N$_3$, NHAc, NHCOCF$_3$, wherein B is covalently bound to W at a substituent selected from the group consisting of Z, U—(CH$_2$)$_r$ and U—(CH$_2$)$_q$;

X, Y, Z=CH$_2$, N, O, S, SO, or SO$_2$;

U=O or —CH$_2$;

Q=H or —X—(CH$_2$)$_q$B;
R$^4$=H, OH, or F;
R$^5$=H, or CH$_2$—R$^4$;
R$^6$=H, OH, NHAc, or NHCOCF$_3$;
R$^7$ and R$^8$ may independently=H, —COR$^{12}$, —CH$_2$—O—(CH$_2$)$_s$,—SO$_2$—(CH$_2$)$_s$—NHG, —CH$_2$—O—(CH$_2$)$_s$—NH—(CH$_2$)$_s$—CH(NHG)—COOR$_1$, —CH$_2$—O—(CH$_2$)$_s$—CHO, —CH$_2$—O—(CH$_2$)$_s$—(CHR$^{13}$)$_s$—(CH$_2$R$^{13}$), wherein s is an integer of from 1–10, or R$^7$ and R$^8$ taken together form a five or six membered ring;
R$^9$, R$^{10}$ are independently H or OH, or R$^9$ and R$^{10}$ taken together form an oxo group;
R$^{11}$=H, 1–6C alkyl, halogen, OH, O-alkyl, or O-aryl;
R$^{12}$=OH, 2–10C alkoxy chain, 2–10C alkylamine, peptide, or OM where M is a counterion;
R$^{13}$=OCO—(CH$_2$)$_t$—CH$_3$, wherein t is an integer of from 3–18; and
G=a peptide, —COR$^{14}$ or —SO$_2$R$^{14}$, wherein R$^{14}$=an aryl, alkyl, alkenyl or alkynyl group.

10. The method of claim 9, wherein the compound of formula II binds to a E-selectin receptor.

11. The method of claim 9, wherein A is sialic acid, B is fucose and W is

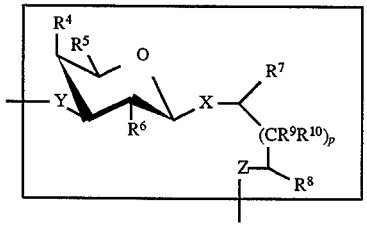

(a)

12. The method of claim 9, wherein the pharmaceutical composition is administered by intravenous injection.

13. The method of claim 9 wherein the method is used to treat inflammation.

14. The method of claim 9 wherein the method is used to treat sepsis.

15. The method of claim 9 wherein the method is used to treat peritonitis.

16. The method of claim 9 wherein the compound is 3-O-(α-Neu5Ac)-β-D-galactopyranoside.

17. The method of claim 9 wherein the compound is 1-O-(3-O-α-carboxy ethyl-β-D-galactopyranosyl)-2-O-(α-L-fucopyranosyl)-3-O-(n-propyl)-propane.

18. The method of claim 9 wherein the compound is 1-Deoxy-1-α-(2-Carboxy-Naphthyl-6-Oxyethyl)-L-Fucose.

19. The method of claim 9 wherein the compound is 2-Carboxy-5-Hydroxy-7-(1-Deoxy-1-α-Fucosyl-Ethyleneoxy)-4-Methoxy Isoflavone.

20. The method of claim 9 wherein the compound is 3,7-Di-(1-Deoxy-1-α-Fucosyl-Ethyleneoxy)-2-Naphthoic Acid.

21. The method of claim 9 wherein the compound is 3,5-Di-(1-Deoxy-1-α-Fucosyl-Ethyleneoxy)-2-Naphthoic Acid.

22. The method of claim 9 wherein the compound is 6-(1-Deoxy-1-α-Fucosyl-Ethyleneoxy)-α-Methyl-2-Naphthoacetic Acid Methyl Ester.

23. The method of claim 9 wherein the compound is 6-Glyceroxy-α-Methyl-2-Naphthoacetic Acid Methyl Ester.

24. The method of claim 9 wherein the compound is 1-Deoxy-1-α-(p-Carboxy-Phenoxyethyl)-L-Fucose.

25. The method of claim 9 wherein the compound is 1-Deoxy-1-α-(o-Carboxy-Phenoxyethyl)-L-Fucose.

26. The method of claim 9 wherein the compound is 1-Deoxy-1-α-(m-Carboxy-Phenoxyethyl)-L-Fucose.

27. The method of claim 9 wherein the compound is 1-Deoxy-1-α-(m-Carboxy-Phenylethyl)-L-Fucose-Phenylalanine Amide.

28. The method of claim 9 wherein the compound is 1-Deoxy-1-α-(p-Carboxy-Phenylethyl)-L-Fucose-Phenylalanine Amide.

29. The method of claim 9 wherein the compound is 1-Deoxy-1-α-(o-Carboxy-Phenylethyl)-L-Fucose-Phenylalanine Amide.

30. The method of claim 9 wherein the compound is 6-O-sulfo-hexanyl-α-L-fucopyranoside.

31. The method of claim 9, wherein M is a metal ion.

32. A compound as in claim 1, wherein the compound is 3-O-(α-Neu5Ac)-β-D-galactopyranoside.

33. A compound as in claim 1, wherein the compound is 1-O-(3-O-α-carboxy ethyl-β-D-galactopyranosyl)-2-O-(α-L-fucopyranosyl)-3-O-(n-propyl)propane.

34. A compound as in claim 1, wherein the compound is 1-Deoxy-1-α-(2-Carboxy-Naphthyl-6-Oxyethyl)-L-Fucose.

35. A compound as in claim 1, wherein the compound is 2-Carboxy-5-Hydroxy-7-(1-Deoxy-1-α-Fucosyl-Ethyleneoxy)-4-Methoxy Isoflavone.

36. A compound as in claim 1, wherein the compound is 3,7-Di-(1-Deoxy-1-α-Fucosyl-Ethyleneoxy)-2-Naphthoic Acid.

37. A compound as in claim 1, wherein the compound is 3,5-Di-(1-Deoxy-1-α-Fucosyl-Ethyleneoxy)-2-Naphthoic Acid.

38. A compound as in claim 1, wherein the compound is 6-(1-Deoxy-1-α-Fucosyl-Ethyleneoxy)-α-Methyl-2-Naphthoacetic Acid Methyl Ester.

39. A compound as in claim 1, wherein the compound is 6-Glyceroxy-α-Methyl-2-Naphthoacetic Acid Methyl Ester.

40. A compound as in claim 1, wherein the compounds 1-Deoxy-1-α-(p-Carboxy-Phenoxyethyl)-L-Fucose.

41. A compound as in claim 1, wherein the compound is 1-Deoxy-1-α-(o-Carboxy-Phenoxyethyl)-L-Fucose.

42. A compound as in claim 1, wherein the compound is 1-Deoxy-1-α-(m-Carboxy-Phenoxyethyl)-L-Fucose.

43. A compound as in claim 1, wherein the compound is 1-Deoxy-1-α-(m-Carboxy-Phenylethyl)-L-Fucose-Phenylalanine Amide.

44. A compound as in claim 1, wherein the compound is 1-Deoxy-1-α-(p-Carboxy-Phenylethyl)-L-Fucose-Phenylalanine Amide.

45. A compound as in claim 1, wherein the compound is 1-Deoxy-1-α-(o-Carboxy-Phenylethyl)-L-Fucose-Phenylalanine Amide.

46. A compound as in claim 1, wherein M is a metal ion.

47. The compound 6-O-sulfo-hexanyl-α-L-fucopyranoside.

48. A method of inhibiting P-selectin binding in a subject in need thereof, comprising administering a therapeutically effective amount of the compound of claim 47.

* * * * *